(12) United States Patent
Chellquist et al.

(10) Patent No.: US 8,716,270 B2
(45) Date of Patent: May 6, 2014

(54) POLYMORPHIC AND AMORPHOUS SALT FORMS OF SQUALAMINE DILACTATE

(75) Inventors: Eric Chellquist, Douglassville, PA (US); Mary Doubleday, Snohomish, WA (US); Charles W. Gilbert, Pottstown, PA (US); Xuehai Zhang, Ellicott City, MD (US); Michael McLane, Lansdale, PA (US); Kyle Armbruster, Douglassville, PA (US); Roy C. Levitt, Miami, FL (US)

(73) Assignee: OHR Pharmaceutical Inc., New York, NY (US)

( * ) Notice: Subject to any disclaimer, the term of this patent is extended or adjusted under 35 U.S.C. 154(b) by 72 days.

(21) Appl. No.: 13/166,911

(22) Filed: Jun. 23, 2011

(65) Prior Publication Data

US 2012/0022035 A1 Jan. 26, 2012

Related U.S. Application Data

(62) Division of application No. 11/410,098, filed on Apr. 25, 2006, now Pat. No. 7,981,876.

(60) Provisional application No. 60/674,531, filed on Apr. 25, 2005.

(51) Int. Cl.
*A61K 31/56* (2006.01)
*C07J 41/00* (2006.01)

(52) U.S. Cl.
USPC .......................................... 514/182; 552/521

(58) Field of Classification Search
USPC .......................................... 514/182; 552/521
See application file for complete search history.

(56) References Cited

U.S. PATENT DOCUMENTS 5,716,960 A  2/1998  Kennedy et al.

FOREIGN PATENT DOCUMENTS

WO  WO 03080027 A1 * 10/2003
WO  WO 2005046589 A2 * 5/2005

OTHER PUBLICATIONS

Anonymous, "Squalamine Lactate (MSI-1256F)", [on line] [retrieved on Oct. 16, 2006]. Retrieved from the internet: < URL: http://www.genaera.com/ARVO2004/images/slide02.gif>, pp. 1-2; (XP002403215).
Bhargava et al., "A Phase I and Pharmacokinetic Study of Squalamine, a Novel Antiangiogenic Agent, in Patients with Advanced Cancers," Clinical Cancer Research 7(12): 3912-3919 (2001); (XP002403213).
Brittain, "Polymorphism in Phamaceutical Solids", (1999), Marcel Dekker, Inc., New York, pp. 235-238.
Database ChemIDplus Advanced, "Squalamine Lactate," [on-line] [retrieved on Sep. 10, 2004]. Retrieved from the Internet: < URL: http://chem.sis.nlm.nih.gov/.chemidplus/jsp/common/ChemFull. jsp?MW=718.0469>, pp. 1-2; (XP002403216).
Examiner's Report for Australian Patent Application No. 2006239811, dated Feb. 9, 2011.
Herbst et al., "A Phase I/IIA Trial of Continuous Five-Day Infusion of Squalamine Lactate (MSI-1256F) Plus Carboplatin and Paclitaxel in Patients with Advanced Non-Small Cell Lung Cancer," Clinical Cancer Research 9(11): 4108-4115 (2003); (XP002403212).
Li et al., "Determination of Degradation Products of Squalamine Lactate Using LC/MS," Journal of Pharmaceutical and Biomedical Analysis 32(1): 85-96 (2003); (XP002403214).
Official Communication for European Patent Application No. 06751251.7, dated Apr. 26, 2010.

* cited by examiner

*Primary Examiner* — Sarah Pihonak
(74) *Attorney, Agent, or Firm* — Morgan, Lewis & Bockius LLP

(57) ABSTRACT

The invention relates to select squalamine salts, methods of their synthesis, their therapeutic use and their advantages relating to manufacturing, product stability and toxicity. More specifically, this application is directed to various forms of the dilactate salt of squalamine and their utility in inhibiting neovascularization and endothelial cell proliferation.

4 Claims, 17 Drawing Sheets

POLYMORPHIC AND AMORPHOUS SALT FORMS OF SQUALAMINE DILACTATE

CROSS REFERENCE TO RELATED APPLICATIONS

This application is a divisional of application Ser. No. 11/410,098, filed Apr. 25, 2006, now U.S. Pat. No. 7,981,876 which claims priority to Provisional Application 60/674,531, filed Apr. 25, 2005, which are hereby incorporated by reference in their entireties. This application is related to U.S. patent application Ser. No. 10/268,660 (filed Oct. 11, 2002) and to U.S. Pat. No. 5,192,756 (issued Mar. 9, 1993), U.S. Pat. No. 6,262,283 (issued Jul. 17, 2001) and U.S. Pat. No. 6,610,866 (issued Aug. 26, 2003), each of which is incorporated in its entirety by reference.

FIELD OF THE INVENTION

This application is directed to select squalamine salts, methods of their synthesis, their therapeutic use and their advantages relating to manufacturing, product stability and toxicity. More specifically, this application is directed to various forms of the dilactate salt of squalamine and their utility in inhibiting neovascularization and endothelial cell proliferation.

BACKGROUND OF THE INVENTION

Several aminosterol compositions have been isolated from the liver of the dogfish shark, *Squalus acanthias*. One such aminosterol is squalamine (3β-(N-[3-aminopropyl]-1,4-butanediamine)-7α, 24R-dihydroxy-5α-cholestane-24-sulfate), the chemical structure of which is shown in FIG. 1. This aminosterol, which includes a sulfate group at the C-24 position, is the subject of U.S. Pat. No. 5,192,756 to Zasloff et al., which describes squalamine's antibiotic properties.

Since its discovery, however, several other interesting properties of squalamine have been revealed. Most notably, as described in U.S. Pat. No. 5,792,635 (issued Aug. 11, 1998) and U.S. Pat. No. 5,721,226 (issued Feb. 24, 1998), which are incorporated in their entirety by reference, squalamine may inhibit the growth of endothelial cells and therefore function as an antiangiogenic agent. The use of squalamine as an antiangiogenic agent for the treatment of neovascularization in the eye and for the treatment of cancers is disclosed in U.S. patent application Ser. No. 09/985,417 (filed Nov. 24, 1998) and U.S. Pat. No. 6,147,060 (issued Nov. 14, 2000) and U.S. Pat. No. 6,596,712 (issued Jul. 22, 2003) which are also incorporated in their entirety by reference.

Methods for synthesizing squalamine have been described in, for example, U.S. Pat. No. 6,262,283 (issued Jul. 17, 2001), U.S. Pat. No. 6,610,866 (issued Aug. 26, 2003), U.S. Pat. No. 5,792,635 (issued Aug. 11, 1998) and in U.S. patent application Ser. No. 10/268,660. These U.S. patents and patent applications are incorporated in their entirety by reference.

Although squalamine has been previously reported to inhibit the proliferation of endothelial cells and therefore found to be useful as an angiogenesis inhibitor, a need still exists for forms of squalamine that can be readily administered to patients, especially in the form of therapeutically active, soluble salts that exhibit thermal stability upon storage and minimal toxicity and for economical methods for the manufacture of these salts. Accordingly, the identification of salts of squalamine which satisfy these requirements and which specifically inhibit angiogenesis, is an object of this invention.

SUMMARY OF THE INVENTION

The present invention relates to various salt forms of squalamine that inhibit endothelial cell proliferation and therefore regulate and/or modulate angiogenesis. The invention also relates to compositions which contain these salts, and methods of their use to treat angiogenesis-dependent diseases and conditions, such as, for example, cancer, tumor growth, atherosclerosis, age related macular degeneration, diabetic retinopathy, retinal ischemia, macular edema and inflammatory diseases in mammals, particularly humans.

An aspect of the invention is an amorphous form or crystalline form of the dilactate salt of squalamine (3β-(N-[3-aminopropyl]-1,4-butanediamine)-7α,24R-dihydroxy-5α-cholestane-24-sulfate).

In an embodiment of the invention, the crystalline form of the dilactate salt exists as a solvate. In another embodiment the crystalline form exists as a hydrate and in a further embodiment the dilactate salt exists as a solvate and a hydrate.

Another aspect of the invention is a method of treating or preventing cancer in a mammal in need of such treatment, comprising administering to said mammal a therapeutically effective amount of the amorphous or crystalline forms of the dilactate salt.

Another aspect of the invention is a method of treating or preventing neovascularization in a mammal in need of such treatment, comprising administering to said mammal a therapeutically effective amount of the amorphous or crystalline forms of the dilactate salt.

In select embodiments, the neovascularization is in the eye, in the gut or in the cardiovascular system.

In preferred embodiments, the neovascularization in the eye results from age related macular degeneration, diabetic retinopathy, an ocular tumor, central retinal vein occlusion, diabetic macular edema (DME) or pathologic myopia.

In a preferred embodiment, the mammal is a human.

In an embodiment, the therapeutically effective amount is about 0.01 to about 10 mg/kg body weight, and more preferably, about 0.01 to about 1 mg/kg body weight.

In an embodiment, the crystalline form of the dilactate salt is characterized by an X-ray powder diffraction pattern having major diffraction angles.

Another aspect of the invention is a process for the preparation of a crystalline form of squalamine dilactate from a non-crystalline form comprising dissolving the non-crystalline squalamine dilactate in a solvent system containing at least two solvents, followed by supersaturating the solvent system until the squalamine dilactate crystallizes from the solvent system. In different embodiments, supersaturation may occur by cooling the solvent system, reducing the volume of the solvent system, adding an additional amount of at least one of the solvents of the at least two solvents or a combination thereof.

In a preferred embodiment, at least one solvent of the at least two solvents is 2-propanol, ethanol, water or 2-butanol.

Another embodiment of the invention comprises a new method for the production of crystallized squalamine dilactate as part of the manufacturing process that removes the need for a HPLC purification step.

DETAILED DESCRIPTION OF THE INVENTION

Definitions

As used herein, the term "amorphous" refers to a form of a compound that lacks a distinct crystalline structure.

As used herein, the term "polymorphic" refers to one of the crystalline forms of a compound or to a compound that has more than one crystalline form.

As used herein, the term "organic alcohol" refers to an organic compound with one or more attached hydroxyl groups.

As used herein, the term "solvate" refers to a crystalline form of a squalamine that contains solvent molecules as part of the crystal structure. In this case the solvent is not water.

As used herein, the term "hydrate" refers to a crystalline form of a squalamine that contains water molecules as part of the crystal structure.

Figure 1:
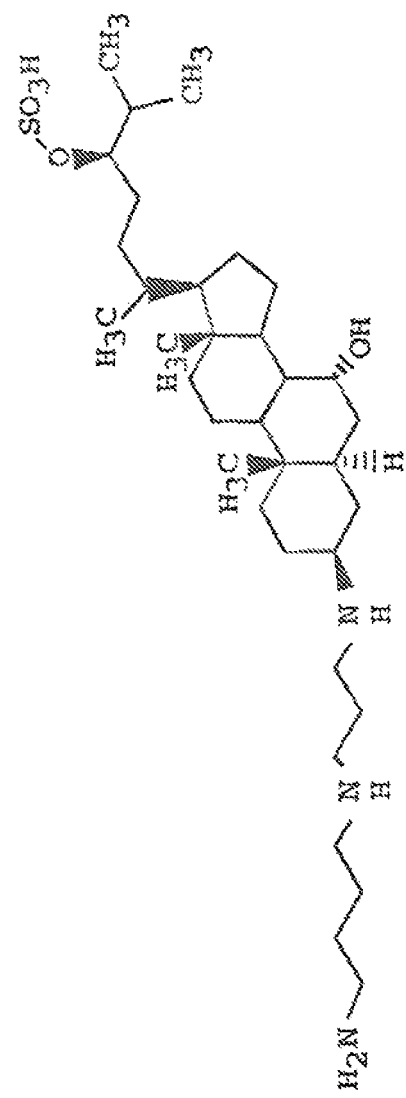
FIG. 1 shows the structure of squalamine.

As used herein, the term "squalamine" includes the compound shown in FIG. 1 with the chemical name 3β-(N-[3-aminopropyl]-1,4-butanediamine)-7α,24R-dihydroxy-5α-cholestane-24-sulfate.

As used herein, the term "aminosterol" refers to a compound with at least one hydroxyl and one amino group directly or indirectly attached to a steroid nucleus. Squalamine is an example of an aminosterol.

As used herein, the term "angiogenesis" refers to the formation of new blood vessels, and an angiogenic is a compound that promotes this activity.

As used herein, the term "antiangiogenic" refers to the prevention of the formation of new blood vessels or the destruction of newly formed blood vessels, and includes an agent that exhibits one or both of these properties.

As used herein, the term "neovascularization" refers to new blood vessel formation in abnormal tissue (as, for example, in a tumor) or in abnormal positions (as, for example, in some conditions of the eye).

As used herein, the term "macular degeneration" is intended to encompass all forms of macular degeneration and includes a gradual loss of central vision usually affecting both eyes that occurs especially in the elderly. A slowly progressing form of macular degeneration, usually referred to as the dry form, is marked especially by the accumulation of yellow deposits in the macula lutea and the thinning of the macula lutea. A rapidly progressing form of macular degeneration, usually referred to as the wet form, is marked by scarring produced by bleeding and fluid leakage from new blood vessels formed below the macula lutea. Macular degeneration may exist as either the wet form or the dry form.

As used herein, the term "diabetic retinopathy" includes retinal changes occurring in long-term diabetes and is characterized by punctate hemorrhages from newly formed blood vessels in the retina, microaneurysms and sharply defined waxy exudates.

As used herein, a "therapeutically effective" amount is an amount of an agent or a combination of two or more agents, which inhibits, totally or partially, the progression of the condition or alleviates, at least partially, one or more symptoms of the condition. A therapeutically effective amount can also be an amount that is prophylactically effective. The amount that is therapeutically effective will depend upon the patient's size and gender, the condition to be treated, the severity of the condition and the result sought. For a given patient, a therapeutically effective amount can be determined by methods known to those of skill in the art.

General

Squalamine has been shown to exhibit antiangiogenic and antimicrobial properties and is useful for the treatment of diseases associated with the growth of new blood vessels such as solid tumor growth and metastasis, atherosclerosis, age related macular degeneration, diabetic retinopathy, neovascular glaucoma, retinal ischemia, macular edema, inflammatory diseases and the like in an animal, preferably in a mammal and more preferably, in a human.

The three basic nitrogen atoms present in the spermidine side chain of squalamine form salts when treated with various acids. One nitrogen atom in the side chain is neutralized by the sulfonic acid at C24 while the other two nitrogen atoms are free to form salts with an added acid. Such squalamine salts include, but are not limited to, dihydrochloride, diacetate, ditrifluoroacetate, digluconate and dilactate. A comparison of various squalamine salts based on their toxicity and stability show the dilactate salt to be a preferred salt. An embodiment of the invention relates to the amorphous dilactate salt form of squalamine. As described below, the dilactate salt can be prepared in an amorphous form through ion exchange chromatography followed by lyophilization or in various crystalline forms by precipitation from different alcoholic solvents. Another aspect of the invention relates to methods for the preparation of the amorphous and the crystalline forms of squalamine dilactate. The complete X-ray structure of the dilactate salt crystallized from 2-propanol has been determined, confirming the stereochemistry at the asymmetric centers of the squalamine molecule as 3β, 5α, 7α and 24 R.

Another embodiment of the invention relates to the various crystalline forms of squalamine dilactate. One particular embodiment is the crystalline form of squalamine dilactate precipitated from 2-propanol which is characterized by an X-ray powder diffraction pattern having major diffraction peaks at 12.5, 16.6 and 18.8 degrees. Another particular embodiment relates to the crystalline form of squalamine dilactate precipitated from ethanol which is characterized by an X-ray powder diffraction pattern having major diffraction peaks at 10.2, 13.0 and 16.6 degrees. Another particular embodiment relates to the crystalline form precipitated from 2-butanol which is characterized by an X-ray powder diffraction pattern having major diffraction peaks at 13.1, 17.7 and 18.3 degrees. Another particular embodiment relates to the crystalline form precipitated from ethanol-water which is characterized by an X-ray powder diffraction pattern having major diffraction angles of 12.6, 15.7 and 18.8 degrees. The crystalline forms of squalamine dilactate may exist as solvates, where solvent molecules are incorporated within the crystal structure. As an example, when the solvent contains ethanol, the crystal may contain ethanol molecules. In another embodiment, the solvate may contain an water, and the crystal may be a hydrate containing water in the crystal structure. In another embodiment the crystal may be both a solvate and a hydrate.

Another embodiment of the invention comprises a new method for the production of recrystallized squalamine dilactate. This new method utilizes the method described in U.S. Pat. No. 6,262,283 to produce a hydroxy-protected ketosterol 1 (e.g., compound 36 where the protecting group (PG) is —OC(O)-Ph); which is then reacted with azidospermidine to produce the corresponding imine 2; followed by reduction with, for example, $NaBH_4$, to produce the azidoaminosterols 3 as a mixture of protected and unprotected 7-alcohols; followed by direct treatment with methanolic potassium hydroxide, followed by hydrogenation in the presence of Raney nickel, to produce crude squalamine. Rather than purification by HPLC and conversion to the dilactate salt by ion exchange chromatography, the crude squalamine is dissolved in ethanol and a two-fold excess of lactic acid is added. The crystalline squalamine dilactate 4 is then precipitated out of solution by the addition of water and, optionally, squalamine dilactate seed crystals. Final purification is then achieved by one or more recrystallizations from aqueous ethanol, preferably containing at least 4% water. This new process produces a better yield and a cleaner product than older methods and results in a considerable cost saving due to the elimination of the HPLC purification step.

The squalamine salts of the invention, and in particular, the squalamine dilactate in any of its forms, may be administered alone or as part of a pharmaceutical composition. Pharmaceutical compositions for use in vitro or in vivo in accordance with the present invention may be formulated in a conventional manner using one or more physiologically acceptable carriers comprising excipients and auxiliaries that facilitate processing of the active compounds into preparations which can be used pharmaceutically. Proper formulation is dependent upon the route of administration chosen. Examples of carriers or excipients include, but are not limited to, calcium carbonate, calcium phosphate, various sugars, starches, cellulose derivatives, gelatin and polymers such as polyethylene glycols.

One example of a pharmaceutical carrier for the squalamine salts of the invention is a cosolvent system comprising benzyl alcohol, a nonpolar surfactant, a water-miscible organic polymer and an aqueous phase. The proportions of the co-solvent system may be varied considerably without adversely affecting the composition's solubility and toxicity characteristics. Furthermore, the identity of the cosolvent components may be varied: for example, other low-toxicity, nonpolar surfactants may be used instead of polysorbate 80; the fraction size of polyethylene glycol may be varied; and/or other biocompatible polymers may replace polyethylene glycol, e.g., polyvinyl pyrrolidone and sugars or polysaccharides, e.g., dextrose.

In addition to carriers, the pharmaceutical compositions of the invention may also optionally include stabilizers, preservatives and/or adjuvants. For examples of typical carriers, stabilizers and adjuvants known to those of skill in the art, see *Remington: The Science and Practice of Pharmacy*, Lippincott, Williams & Wilkins (2000), which is incorporated by reference in its entirety.

Optionally, other therapies known to those of skill in the art may be combined with the administration of the squalamine salts of the invention. More than one aminosterol may be present in a single composition.

In vivo administration of squalamine salts of the invention can be effected in one dose, multiple doses, continuously or intermittently throughout the course of treatment. Doses range from about 0.01 mg/kg to about 10 mg/kg, preferably between about 0.01 mg/kg to about 1 mg/kg, and most preferably between about 0.1 mg/kg to about 1 mg/kg in single or divided daily doses. Methods of determining the most effective means and dosages of administration are well known to those of skill in the art and will vary with the composition used for therapy, the purpose of the therapy, the target cell being treated and the subject being treated. Single or multiple administrations can be carried out with the dose level and pattern being selected by the treating physician.

Pharmaceutical compositions containing the squalamine salts of the invention can be administered by any suitable route, including oral, rectal, intranasal, topical (including transdermal, aerosol, ocular, buccal and sublingual), parenteral (including subcutaneous, intramuscular, intravenous), intraperitoneal and pulmonary. It will be appreciated that the preferred route will vary with the condition and age of the recipient, and the disease being treated. For treatment of age-related macular degeneration, for example, the preferred routes of administration are topical, subcutaneous, intramuscular and/or intravenous.

For oral administration, the squalamine salts of the invention can be formulated readily by combining them with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients include, for example, fillers such as sugars, including lactose, sucrose, mannitol, or sorbitol; cellulose preparations such as maize starch, wheat starch, rice starch, potato starch, gelatin, gum tragacanth, methyl cellulose, hydroxypropylmethylcellulose, sodium carboxymethylcellulose and polyvinylpyrrolidone (PVP). If desired, disintegrating agents may be added, such as the cross-linked polyvinyl pyrrolidone, agar, alginic acid or a salt thereof, such as sodium alginate.

Pharmaceutical compositions for topical administration of the squalamine salts of the invention may be formulated in conventional ophthalmologically compatible vehicles, such as, for example, an ointment, cream, suspension, lotion, powder, solution, paste, gel, spray, aerosol or oil. These vehicles may contain compatible preservatives such as benzalkonium chloride, surfactants such as polysorbate 80, liposomes or polymers such as methylcellulose, polyvinyl alcohol, polyvinyl pyrrolidone and hyaluronic acid, which may be used for increasing viscosity. For diseases of the eye, preferred topical formulations are ointments, gels, creams or eye drops containing at least one of the aminosterols of the invention.

For administration by inhalation, the squalamine salts of the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The squalamine salts can be formulated for parenteral administration by injection, e.g., bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as buffers, bacteriostats, suspending agents, stabilizing agents, thickening agents, dispersing agents or mixtures thereof.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides or liposomes. Aqueous injection suspensions may contain substances that increase the viscosity of the suspension, such as sodium carboxymethyl cellulose, sorbitol or dextran. Optionally, the suspension may also contain suitable stabilizers or agents that increase the solubility of the compounds to allow for the preparation of highly concentrated solutions. In a preferred embodiment, the squalamine salts of the invention are dissolved in a 5% sugar solution, such as dextrose, before being administered parenterally.

For injection, the squalamine salts of the invention may be formulated in aqueous solutions, preferably in physiologically compatible buffers such as Hanks's solution, Ringer's solution or physiological saline buffer. For transmucosal administration, penetrants appropriate to the barrier to be permeated are used in the formulation. Such penetrants are generally known in the art.

The squalamine salts may also be formulated in rectal compositions such as suppositories or retention enemas, e.g., containing conventional suppository bases such as cocoa butter or other glycerides.

The squalamine salts may also be combined with at least one additional therapeutic agent. Exemplary agents include, for example, anticancer, antibiotic, antiviral, antiangiogenic or another treatment for neovascularization in the eye.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Preparation of Amorphous Squalamine Dilactate

Crude squalamine was prepared according to the methods described in U.S. Pat. No. 6,262,283, U.S. Pat. No. 6,610,866 and U.S. patent application Ser. No. 10/268,660. The crude squalamine was dissolved in water, acidified with trifluoroacetic acid (TFA) and then purified by reverse phase HPLC using a $C_{18}$ YMC ODS-AQ column or equivalent and a binary solvent system. The HPLC chromatography was performed to collect fractions of product that meet the drug substance specifications. The fractions of pure squalamine TFA salt were concentrated prior to salt conversion.

Conversion of the squalamine TFA salt to squalamine dilactate salt was accomplished by adsorption of the TFA salt to Amberchrom resin or its equivalent. The resin was then washed extensively with 1% acetonitrile in water, sodium bicarbonate and 1% acetonitrile in water; and finally with an excess of L-(+) lactic acid dissolved in water. The dilactate salt of squalamine was eluted with a stepwise increase in the percentage of acetonitrile in water. The fractions containing squalamine dilactate were pooled, concentrated and lyophilized. Analysis of the material for lactic acid and squalamine showed a ratio of two moles of lactic acid per mole of squalamine. The characterization of the lyophilized squalamine dilactate is described below.

X-Ray Diffraction Powder Pattern

Figure 2:
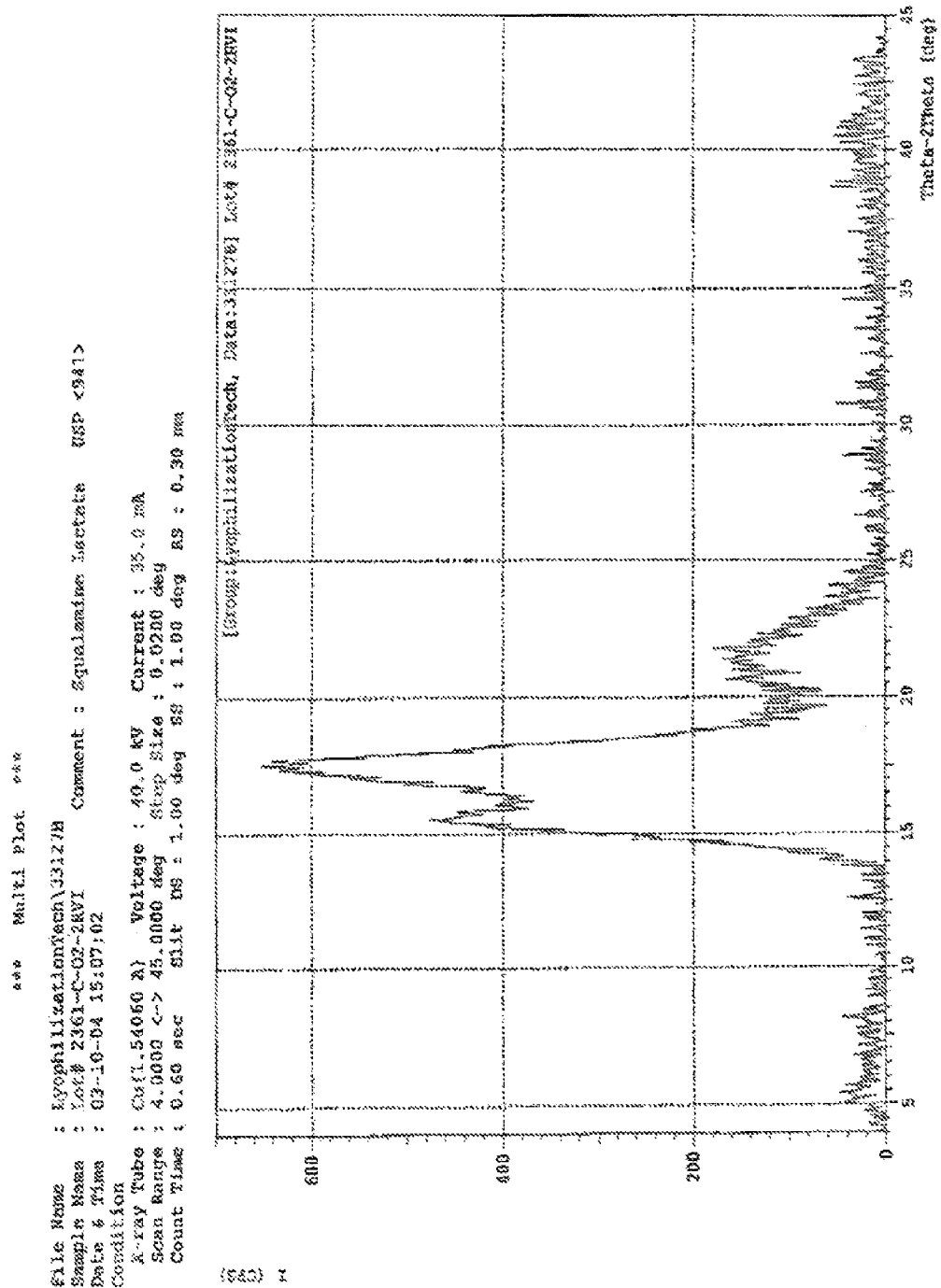
FIG. 2 shows the x-ray diffraction powder pattern for lyophilized squalamine dilactate.

The powder x-ray diffraction scans on a sample of lyophilized squalamine dilactate were performed from 4.0 to 45.0 degrees (2θ in compliance with USP Method <941>) while a polycarbonate film covered the sample. The pertinent data is shown in FIG. 2 and summarized in the Table below. These data show an amorphous halo with a few discrete peaks indicating a low or partial crystallinity.

|  | Angle (° theta-2 theta) | | |
| --- | --- | --- | --- |
| Sample Preparation | 15.5-15.6 | 17.3-17.5 | 21.3-21.5 |
| Lyophilized Squalamine | 286 | 391 | 107 |

Thermogravimetric Analysis

Figure 3:
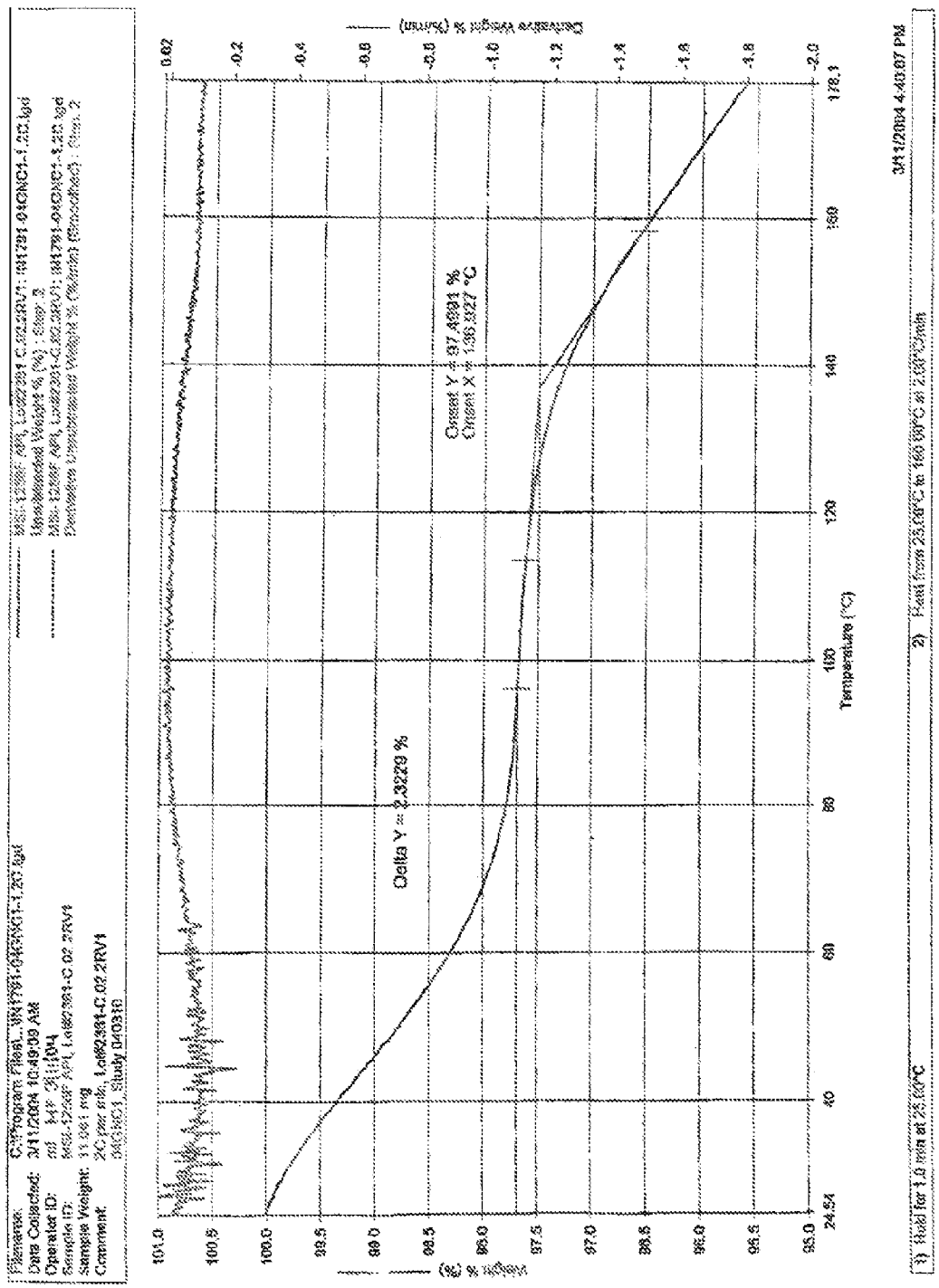
FIG. 3 shows a thermogravimetric scan of the lyophilized squalamine dilactate.

Thermogravimetric analysis involves the determination of the weight of a specimen as a function of temperature as per USP <891>. The samples of lyophilized squalamine dilactate were prepared in a nitrogen atmosphere in a humidity-controlled glovebox. Analyses were completed using a Perkin Elmer TGA7 with TAC 7/DX Instrument Controller and Pyris Software Version 4.01. Nitrogen, NF was used at a flow rate of 20 mL/minute. The samples were warmed at a controlled rate of 10° C. per minute to generate better sensitivity and at 2° C. per minute in order to acquire a better resolution to a final temperature of 180° C. The results for the 2° C. per minute scan are shown in FIG. 3 and the data summarized in the table below. The data exhibit a single weight loss of 2.32% and degradation onset at a temperature of 136.9° C.

| Squalamine Dilactate Preparation | Rate (° C./min) | Primary Mass Loss | Peak of Secondary Mass Loss | Secondary Mass Loss | Onset to Degradation |
|---|---|---|---|---|---|
| Lyophilized Squalamine | 2 | 2.32% | N/A | N/A | 136.9° C. |

Differential Scanning Calorimetry

Figure 4:
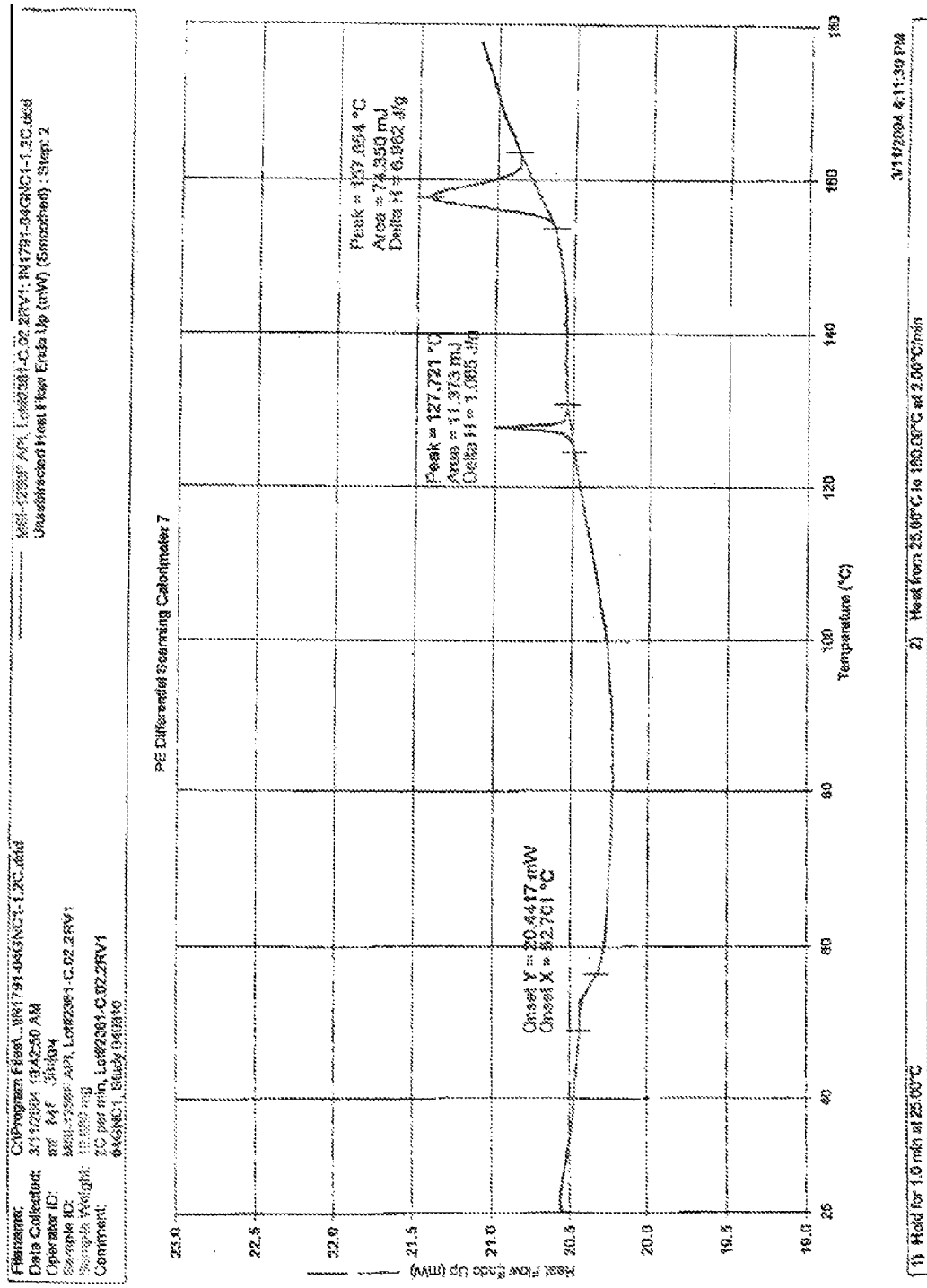
FIG. 4 shows a Differential Scanning calorimeter profile for lyophilized squalamine dilactate.

Samples were analyzed by high temperature differential scanning calorimetry and were run at 2° C. and 10° C. per minute. Thermal transitions acquired during a scan rate of 2° C. per minute are considered to be more accurate and are the calculations reflected in the conclusion. All events listed are endothermic peak temperatures unless otherwise noted. Examples of additional events include an "Exo" indicating an exothermic event or "Tg" which indicates a phase transition. The lack of a notable thermal event on a particular scan is indicated by "none". During analysis of lyophilized squalamine dilactate, an exothermic event was detected at an onset temperature of 52.7° C. during a scan at 2° C. per minute. A phase transition (Tg) event, occurring at a temperature of 62.0° C. during a scan at 10° C. per minute, did not have a corresponding thermal event when scanned at 2° C. per minute. A phase transition is indicative of an amorphous portion of the dried material softening and changing structure. Two endothermic events were observed at peak temperatures of 127.7° C. and 157.7° C. during the scan at 2° C. per minute. The largest change in specific heat associated with an endothermic event for lyophilized squalamine dilactate was a change in specific heat of 8.15 J/g which was observed during the 10° C. per minute scan at a temperature of 166.51° C. The change in specific heat associated with an endothermic event is correlated to the amount of energy required to melt that material. The results of the 2° C. per minute scan are shown in FIG. 4 and summarized in the table below.

| Squalamine Dilactate Preparation | Rate (° C./min) | 1 | 2 | 3 | 4 | 5 |
|---|---|---|---|---|---|---|
| Lyophilized Squalamine | 2 | 52.7 (Exo) | None | 127.7 | 157.7 | none |
|  | 10 | 62.0 (Tg) | 71.3 (Exo) | 98.3 (Exo) | 130.1 | 166.5 |

Example 2

A Study of Local Irritancy of 5-Day Repeated Intravenous Injections of Different Salt Forms (Ditrifluoroacetate, Dilactate, Digluconate, Diacetate) of MSI-1256 (Squalamine) in Mice Summary: Five-day repeated injections of various salt forms of squalamine (2.5 mg/kg/day) caused swelling, bruising and irritation of the mouse-tails. Treatment with squalamine dilactate and squalamine digluconate, was tolerated slightly better than treatment with squalamine diacetate and squalamine ditrifluoroacetate, although swelling, bruising and irritation were observed with all injected salt forms of squalamine administered repeatedly at a dose of 2.5 mg/kg/day using 0.25 mg/mL solutions.

Objective: To determine the local irritancy of 5-day repeated daily intravenous doses of squalamine salt forms in tails of CD-1®BR mice.

Material and Methods: (Animals): Forty-eight male CD-1®BR mice (Charles River Lab). Mean body weight at study initiation was 20.6 gm. (Housing Environment): Mice were housed as groups (maximum 10 mice/box) in plastic mouse boxes with hardwood chip bedding and wire lids. They had access to food (Purina Mouse Chow) and water in bottles ad lib. The boxes were housed in isolator racks that were supplied with one-pass through filtered room air. The room in which the animals were housed was on a 12-hour on/12-hour off light cycle and had controlled temperature (range: 67-76° F.) and humidity (range: 40-70% relative humidity).

Test Articles:
squalamine ditrifluoroacetate, 69.7% active moiety
squalamine diacetate, 80.0% active moiety
squalamine dilactate, 76.0% active moiety
squalamine digluconate, 55.0% active moiety
Magainin-2-amide, positive control
Vehicle: 5% Dextrose in Water (D5W) (Baxter I.V. bag, sterile)

Solution prep: A 0.36 mg/mL solution of squalamine ditrifluoroacetate salt (equivalent to 0.25 mg/mL squalamine ditrifluroacetate active moiety) was prepared in D5W. A 0.31 mg/mL solution of squalamine diacetate salt (equivalent to 0.25 mg/mL squalamine diacetate active moiety) was prepared in D5W. A 0.33 mg/mL solution of squalamine dilactate salt (equivalent to 0.25 mg/mL squalamine dilactate active moiety) was prepared in D5W. A 0.45 mg/mL solution of squalamine digluconate salt (equivalent to 0.25 mg/mL squalamine digluconate active moiety) was prepared in D5W. A 1.0 mg/mL solution of magainin-2-amide (positive control) was prepared in D5W. Protocol: Mice were randomly assigned to six groups (8 mice/group) and received daily intravenous (i.v.) injections of solutions of D5W or squalamine salts in the tail vein for five days (study days 0, 1, 2, 3, and 4). Injectate volumes of 10 mL/kg body weight using D5W or a 0.25 mg/mL solution of squalamine salts resulted in doses of 0 mg/kg/day for the mice in D5W group (Group 1) and 2.5 mg/kg/day of squalamine salt active moiety for all squalamine salt treated mice. One group of eight mice received test article magainin-2-amide (10 mg/kg/day; 10 mL/kg/day of a 1 mg/mL solution), which was previously determined to be local vein irritant, as a positive control. Mice were not injected with test article if severity of bruising or swelling (edema) warranted the omission of the injection. Survival was monitored and clinical signs were observed daily for five days of administration of squalamine salts and four days after the last dose (Study Day 8). Clinical signs of irritancy, edema, and bruising were made on days 1, 2, 3, and 4 approximately 24-hours after each injection and immediately prior to that day's injection. The pHs of the solutions of all test articles except magainin-2-amide were checked on Study Day 3. (The same solutions were used throughout the study so a similar pH on all study days may be assumed).

Results: Animals that were administered repeated intravenous (i.v.) doses of various salt forms of squalamine in the tail vein had irritated, swollen (edema) and/or bruised tails by Study Day 2. The number of mouse tails which were bruised and edematous as well as the severity of bruising and edema was directly related to the number of injections. To assess recovery, tails were observed on Study Day 8, which was four days post-last injection. On Day 8, the tails of mice in Groups 3 and 4 (having received the dilactate and digluconate salt forms, respectively) were slightly irritated and bruised. The tails of mice in Groups 5 and 6 (having received the diacetate and ditrifluoroacetate salt forms, respectively) were similarly irritated and bruised. One (⅛) mouse tail in Group 5 was necrotic. In Group 6, one (⅛) mouse tail fell off, and one (⅛)

mouse tail was also necrotic. Group 2 (positive control) mice showed slight or moderate edema in tails during dosing (⅛, ⅜, ⅝, and ⅝ on Days 1, 2, 3 and 4) and recovered by Day 8. The pHs of all solutions of squalamine salt forms were approximately 6.

Conclusions: Repeated injections of all salt forms of squalamine caused swelling (edema), bruising and irritation of the mouse tails. The clinical symptoms suggest that treatment with squalamine dilactate and squalamine digluconate was tolerated better than treatment with squalamine diacetate and squalamine ditrifluoroacetate. Thus, an unexpected advantage of the squalamine dilactate and squalamine digluconate salts over other tested squalamine salts is less venous irritation, i.e., less toxicity, experienced by the recipient, especially at the site of intravenous administration.

Example 3

Accelerated Stability Study of Four Salt Forms of Squalamine

An accelerated stability study (temperature-based) lasting four weeks was performed on squalamine in four different salt forms. The four salt forms were: dihydrochloride, diacetate, dilactate and D-digluconate. The samples were subjected to temperatures of 40° C., 60° C. and 80° C. The following table summarizes the results of % purity of main peak, squalamine, based on total integrated area. The analysis was performed using reversed-phase HPLC of o-phthaldialdehyde derivatized samples.

TABLE 1

| Salt Form | T = 0 | 4 w 40° C. | 4 w 60° C. | 4 w 80° C. |
|---|---|---|---|---|
| Dihydrochloride | 90.7% | 84.3% | 85.3% | 82.4% |
| Diacetate | 94.4% | 87.3% | 81.5% | 62.9% |
| Dilactate | 91.8% | 80.9% | 80.6% | 70.9% |
| Digluconate | 87.8% | 72.6% | 60.7% | 4.9% |

Table 1 shows how each salt form has degraded over time at elevated temperatures. The results of this stability study indicate that squalamine dilactate is surprisingly stable under increasingly severe conditions, especially compared to the diacetate and digluconate salts. This advantageous stability of the squalamine dilactate salt coupled with its low toxicity (as shown in Example 2) were important factors in selecting the squalamine dilactate salt form for further development.

Example 4

Preparation of Crystalline Squalamine Dilactate from 2-Propanol

A supersaturated solution of amorphous squalamine dilactate was produced by heating an excess of squalamine dilactate to 90° C. in a mixture of 10 ml of 2-propanol plus 100 µl of water. The excess squalamine dilactate was filtered off and the solution was cooled to −20° C. A precipitate of white needles formed, the supernatant was removed and the solid dried in a vacuum desiccator. The resulting crystalline material was observed to be non hygroscopic as it did not gain weight when left at room temperature uncovered for one hour.

Single Crystal X-Ray Diffraction Pattern Determination

Single crystals suitable for X-ray study were obtained from a solution of 2-propanol and water as described above. The biggest crystal, with the dimensions of 0.025, 0.10, and 1.10 mm was chosen for the study. The crystal was mounted on a Nonius Kappa CCD instrument with molybdenum radiation and CCD area detector. The crystal was cooled to 173° K using a nitrogen stream cooled by liquid nitrogen. The preliminary measurements showed that the diffraction was very weak beyond 22 degrees in theta and that the crystal belonged to the monoclinic space group. To enhance the differentiation of chiral isomers, it was decided that the data would be collected in lower crystal system (namely triclinic). The data were collected by exposing the crystal for 500 seconds per degree of crystal rotation. The total data collection took 32 hours. The data were processed to obtain the final intensity of the diffraction pattern and all the unique measurements were kept separate without applying the Friedel law.

The space group analysis showed that there was no systematic absence. The diffraction pattern analysis showed that the crystal belonged to a non-centric space group and a possible two fold symmetry along the b-axis, suggesting that it may belong to P2 space group. All these were consistent with what is expected for a chiral molecule, which cannot belong to centric space group and cannot have mirror or glide symmetries. The intensity analysis showed that the data were becoming weak at the higher angles of theta. The average intensity at the 21-22 degree theta range was just 1.9 times of the average background. However, there were enough strong data to provide the molecular structure with proper absolute configuration (chirality).

The structure was readily solved by direct methods in the space group P2 suggested by the data analyses. Refinement of the structure by least-squares followed by difference Fourier showed the presence of solvent molecules. Many water molecules and one disordered 2-propanol molecule were detected. The occupancies of the molecules were verified by refinement and one water molecule was found to have only half (50%) occupancy. All the non-hydrogen atoms were refined with anisotropic displacement parameters (ADP). Hydrogen atoms connected to carbon and nitrogen atoms were included at calculated positions. For hydroxyl groups and water molecules, only when reasonable atoms were found in difference Fourier, they were included. For the disordered 2-propanol molecule and for oxygen for which no reasonable atom could be located from different Fourier were not included in the calculation. The refinement used 6119 intensity data and refined 612 parameters. The final residual factor (R-factor) was 0.087, which unambiguously proves the structure of the molecule.

There are several polar (electron-deficient) hydrogens at cationic nitrogens and hydroxyl oxygens. There are also several electron rich oxygens at anionic centers. This leads to a network of hydrogen bonding formation. Also, many water molecules join the hydrogen-bonding network. The detailed are described below.

| H-Donor | H-Acceptor | Distance (Å) | Symmetry |
|---|---|---|---|
| O1 | O2W | 2.692 | x, y, z |
| N1(H1A) | O10 | 2.835 | x − 1, y − 1, z |
| N1(H1B) | O9 | 2.842 | x − 1, y − 2, z |
| N1(H1B) | O11 | 2.854 | x − 1, y − 2, z |
| N2(H2A) | O6 | 2.734 | −x, y, 2 − z |
| N2(H2B) | O7 | 2.876 | −x, y − 1, 2 − z |
| N2(H2B) | O8 | 2.835 | −x, y − 1, 2 − z |
| N3(H3C) | O3 | 2.886 | −x, y, 2 − z |
| N3(H3A) | O1W | 2.804 | x − 1, y − 1, z + 1 |
| N3(H3B) | O1S or O1S' | 2.940 or 2.945 | x − 1, y − 1, z + 1 |
| O2W(H3W) | O7 | 2.811 | x, y, z |
| O2W(H4W) | O9 | 2.762 | 1 − x, y − 1, 2 − z |
| O8(H8) | O3W | 2.747 | x, y, z |

| H-Donor | H-Acceptor | Distance (A) | Symmetry |
|---|---|---|---|
| O3W | O4W | 2.777 | x, y, z |
| O3W | O6 | 2.665 | x, 1 + y, z |
| O4W | O10 | 2.749 | x, y, z |
| O4W | O4W | 2.840 | 1 − x, y, 2 − z |
| O11 | O4W | 2.779 | x, 1 + y, z |
| O1S or O1S' | O3W | 2.730 or 2.857 | 1 − x, y, 1 − z |

Figure 5:
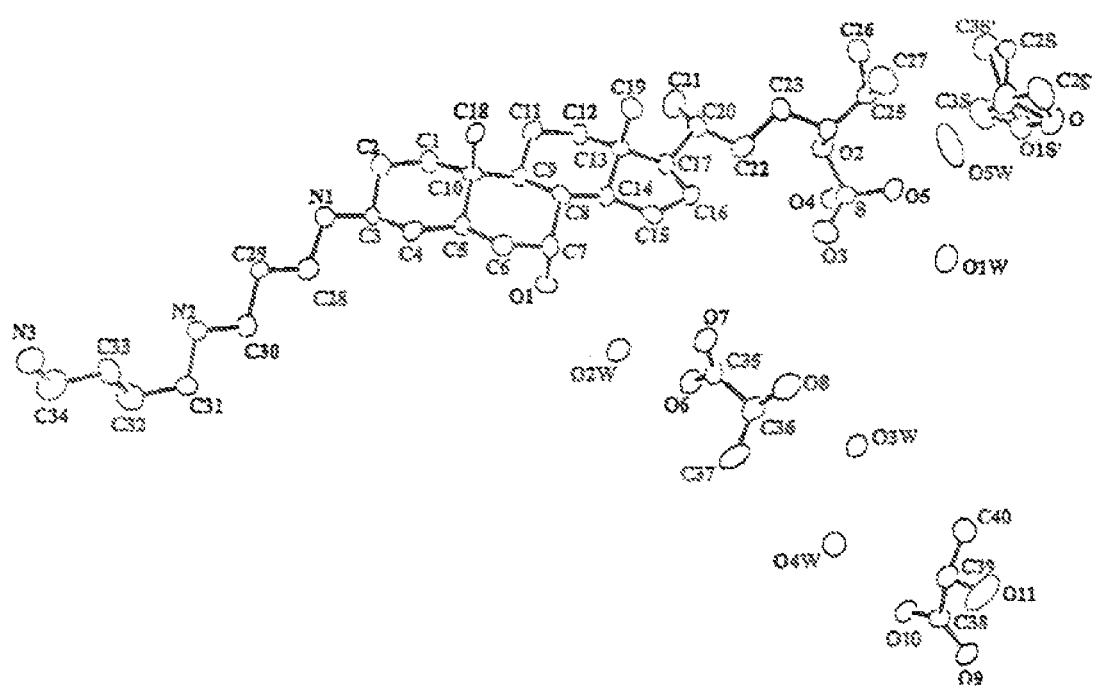
FIG. 5 shows the crystal structure of squalamine dilactate crystallized from 2-propanol.

The distances are given between the non-hydrogen atoms and where available the hydrogens through which the bonding formed are shown in parenthesis. The crystal structure of squalamine dilactate is shown in FIG. 5.

A unit cell was determined from the single crystal X-ray data of the hydrated form. It was monoclinic with P2 symmetry, Z=2, and the following dimensions: a=19.3999 Å, b=6.5443 Å, c=20.9854 Å, alpha=gamma=90°, beta=92.182° and V=2662.3 Å$^3$.

X-Ray Diffraction Powder Pattern

Figure 6:
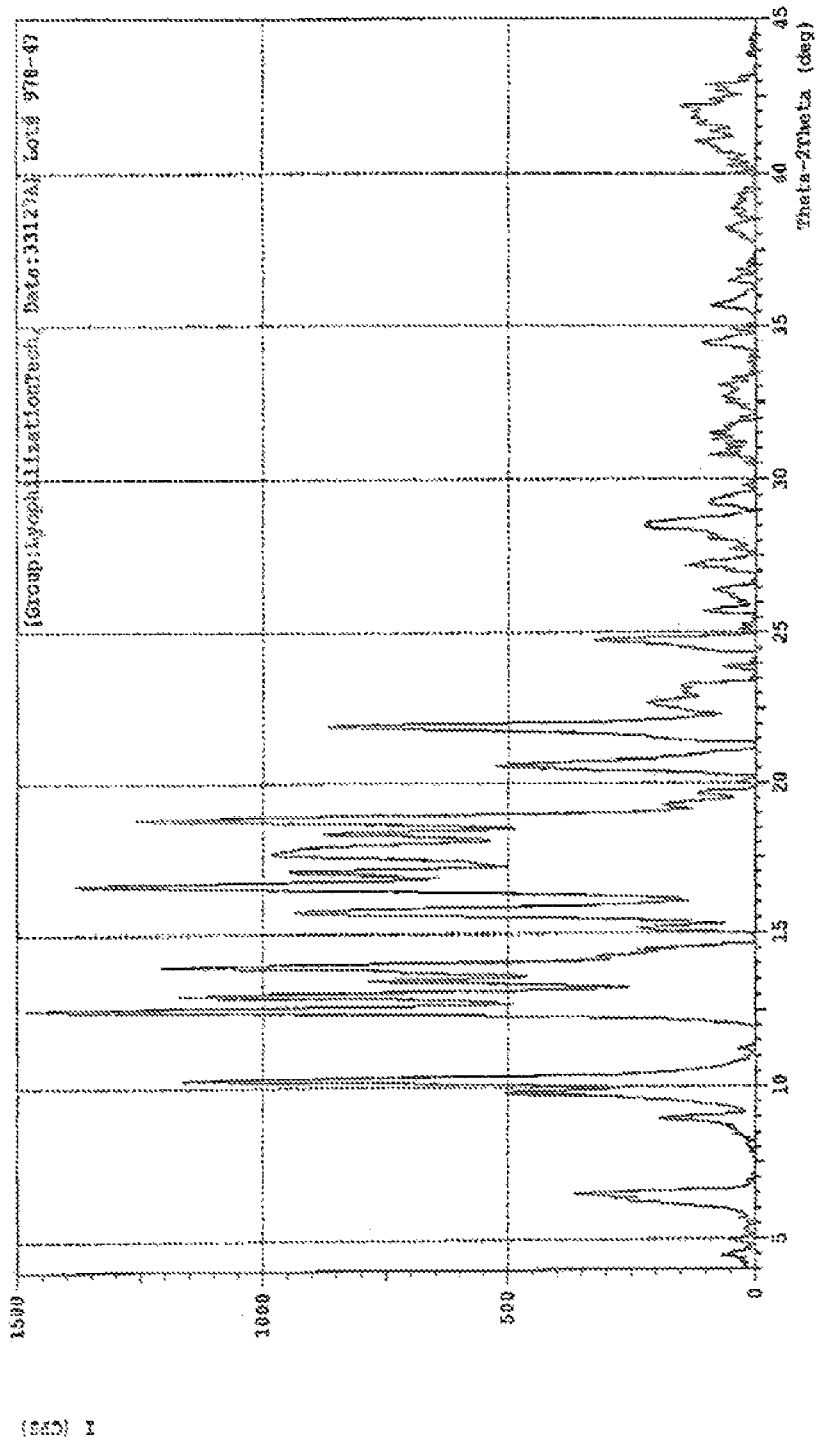
FIG. 6 shows the x-ray diffraction powder pattern for squalamine dilactate crystallized from 2-propanol.

The powder x-ray diffraction scans on a sample of squalamine dilactate crystallized from 2-propanol were performed from 4.0 to 45.0 degrees (2θ in compliance with USP Method <941>) while the sample was covered by a polycarbonate film. The pertinent data, consisting of distinct crystalline peaks is shown in FIG. 6 and indicates a crystalline material.

| Sample Preparation | Angle (° theta-2 theta) | | |
|---|---|---|---|
| | 12.5 | 16.6 | 18.8 |
| Crystallized from 2-propanol/water | 890 | 829 | 756 |

Thermogravimetric Analysis

Figure 7:
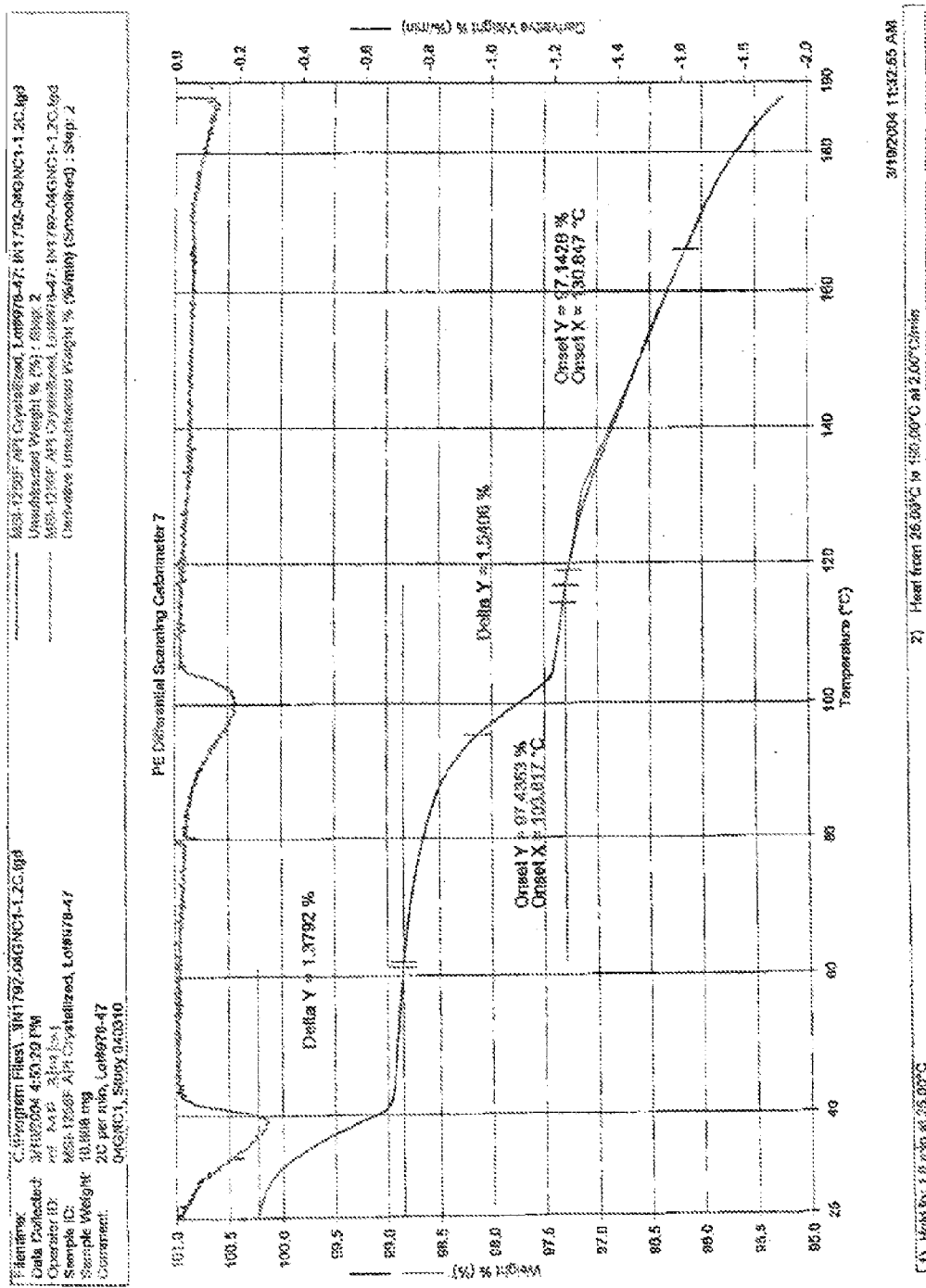
FIG. 7 shows a thermogravimetric scan of the squalamine dilactate crystallized from 2-propanol.

Thermogravimetric analysis involves the determination of the weight of a specimen as a function of temperature as per USP <891>. The samples were prepared in a nitrogen atmosphere in a humidity controlled glovebox. Analyses were completed using a Perkin Elmer TGA7 with TAC 7/DX Instrument Controller and Pyris Software Version 4.01. Nitrogen, NF was used at a flow rate of 20 mL/minute. The samples were warmed at a controlled rate of 10° C. per minute to generate better sensitivity and at 2° C. per minute in order to acquire a better resolution to a final temperature of 180° C. This crystallized material had two distinct volatile weight loss events. The initial event yielded a 1.38% weight loss. The second event yielded an average weight loss of 1.54% with a peak event observed at a temperature of 103.6° C. when tested at 2° C. per minute. The total weight loss incurred by the sample was 2.92%. The two distinct weight loss events suggest that a bound form of water existed within the sample matrix. The initial loss is most likely due to the driving off of volatile constituents adsorbed to the material surface. The second weight loss event occurred due to a release of absorbed water associated with the sample matrix, which was most likely a crystalline hydrate, at a peak temperature of 103.6° C. The second distinct release of moisture from the sample at a specific temperature suggests a breakdown of a large portion of crystalline material. The results for the 2° C. per minute scan are shown in FIG. 7 and the data summarized in the table below.

| Squalamine Dilactate Preparation | Rate (° C./min) | Primary Mass Loss | Peak of Secondary Mass Loss | Secondary Mass Loss | Onset to Degradation |
|---|---|---|---|---|---|
| Crystallized from 2-propanol/water | 2 | 1.38% | 103.6° C. | 1.54% | 130.8° C. |

Differential Scanning Calorimetry

Figure 8:
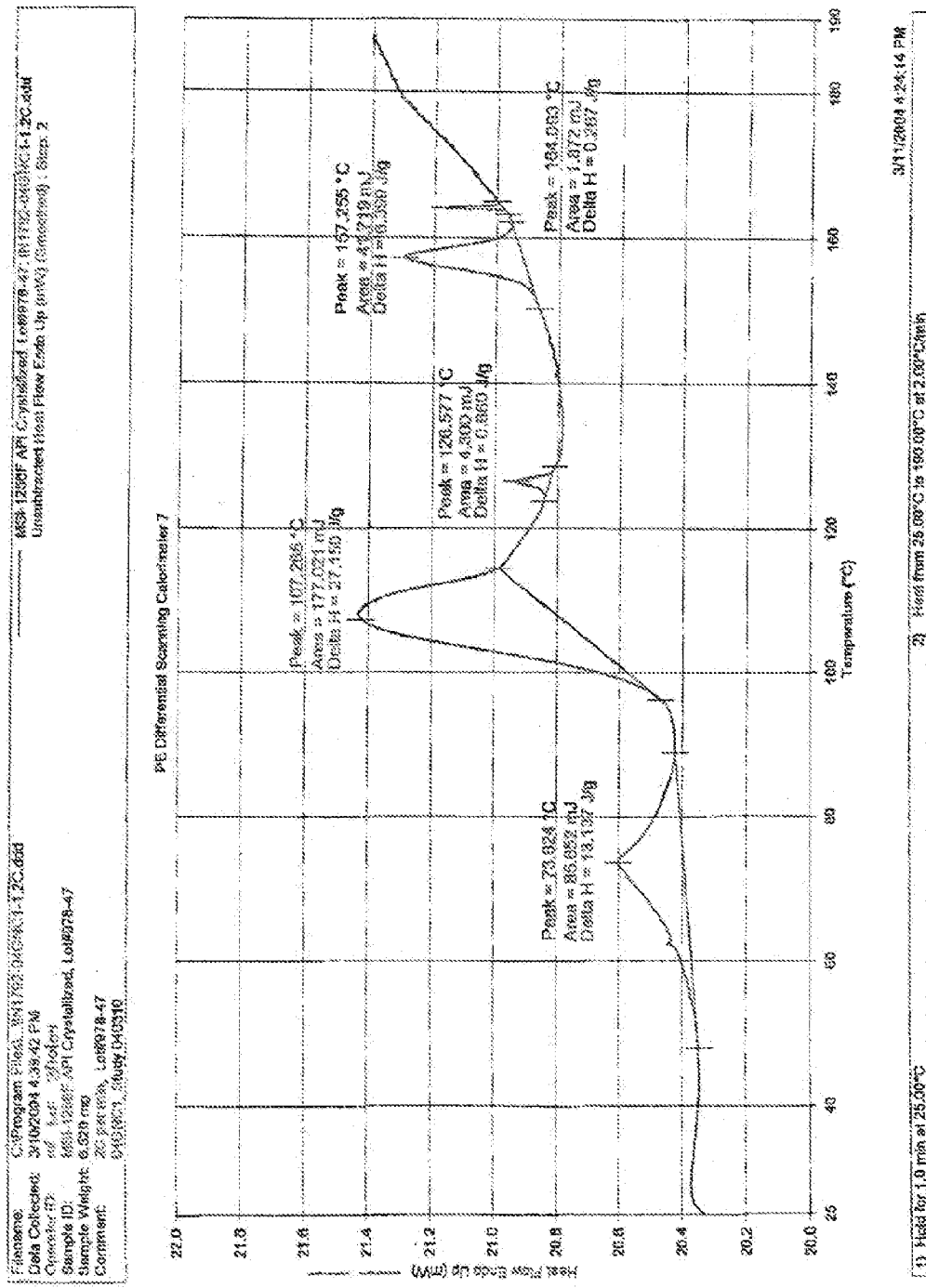
FIG. 8 shows a Differential Scanning calorimeter profile for squalamine dilactate crystallized from 2-propanol.

Samples were analyzed by high temperature differential scanning calorimetry and were run at 2° and 10° C. per minute. Thermal transitions acquired during a scan rate of 2° C. per minute are considered to be more accurate and are the calculations reflected in the conclusion. All events listed are endothermic peak temperatures unless otherwise noted. Examples of additional events include an "Exo" indicating an exothermic event or "Tg"" which indicates a phase transition. The lack of a notable thermal event on a particular scan is indicated by "none". The first thermal event characterized by DSC at 2° C. per minute for this crystallized material was an endothermic event that occurred at a temperature of 73.6° C. Endothermic events are attributable to the initial melt of a crystallized material. The most significant thermal event was an additional endothermic event that occurred at a temperature of 107.3° C. This endothermic event coincides with the peak weight loss temperature of 103.6° C. during the TGA scan of this particular material. Three additional exothermic events occurred at temperatures of 126.6°, 157.3°, and 164.1° C. The results of the 2° C. per minute scan are shown in FIG. 8 and summarized in the table below.

| Squalamine Dilactate Preparation | Rate (° C./min) | 1 | 2 | 3 | 4 | 5 |
|---|---|---|---|---|---|---|
| Crystallized from 2-propanol/water | 2 | 73.6 | 107.3 | 126.6 | 157.3 | 164.1 |
| | 10 | 79.8 | 112.8 | 130.5 | none | 165.6 |

Example 5

Preparation of Crystalline Squalamine Dilactate from Ethanol

A supersaturated solution of amorphous squalamine dilactate was produced by heating an excess of squalamine dilactate to 90° C. in a mixture of 10 ml of ethanol plus 100 μl of water. The excess squalamine dilactate was filtered off and the solution was cooled to −20° C. A precipitate of white needles formed, the supernatant was removed and the solid dried in a vacuum desiccator.

X-ray Diffraction Powder Pattern

Figure 9:
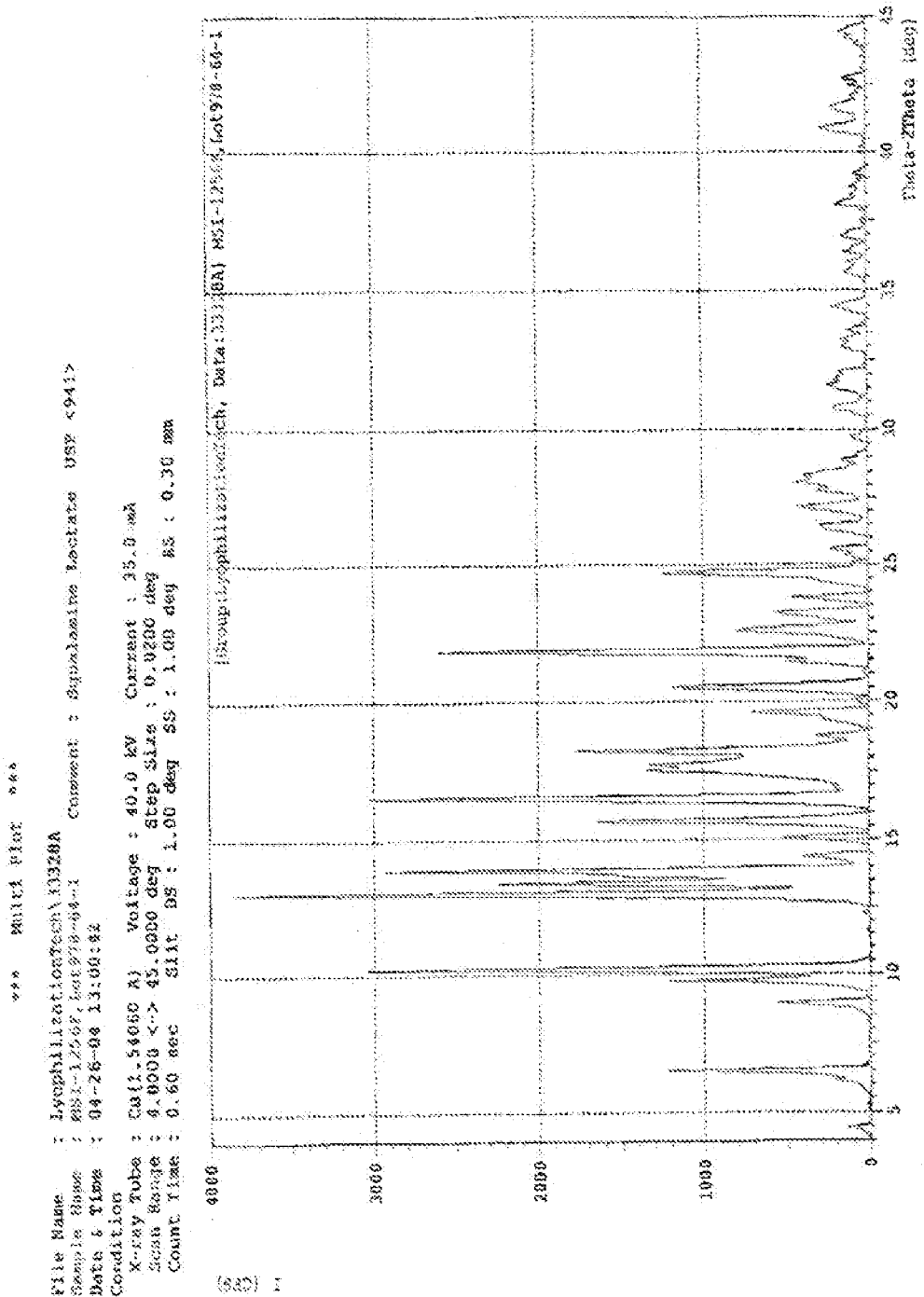
FIG. 9 shows the x-ray diffraction powder pattern for squalamine dilactate crystallized from ethanol.

The powder x-ray diffraction scans on a sample of squalamine dilactate crystallized from ethanol were performed from 4.0 to 45.0 degrees (2θ in compliance with USP Method <941>) while the sample was covered by a polycarbonate film. The pertinent data, consisting of distinct crystalline peaks is shown in FIG. 9 and summarized in the table below and indicates a crystalline material.

|  | Angle (° theta-2 theta) | | |
|---|---|---|---|
| Sample Preparation | 10.2 | 13.0 | 16.6 |
| Crystallized from ethanol/water | 1826 | 2305 | 1817 |

Thermogravimetric Analysis

Figure 10:
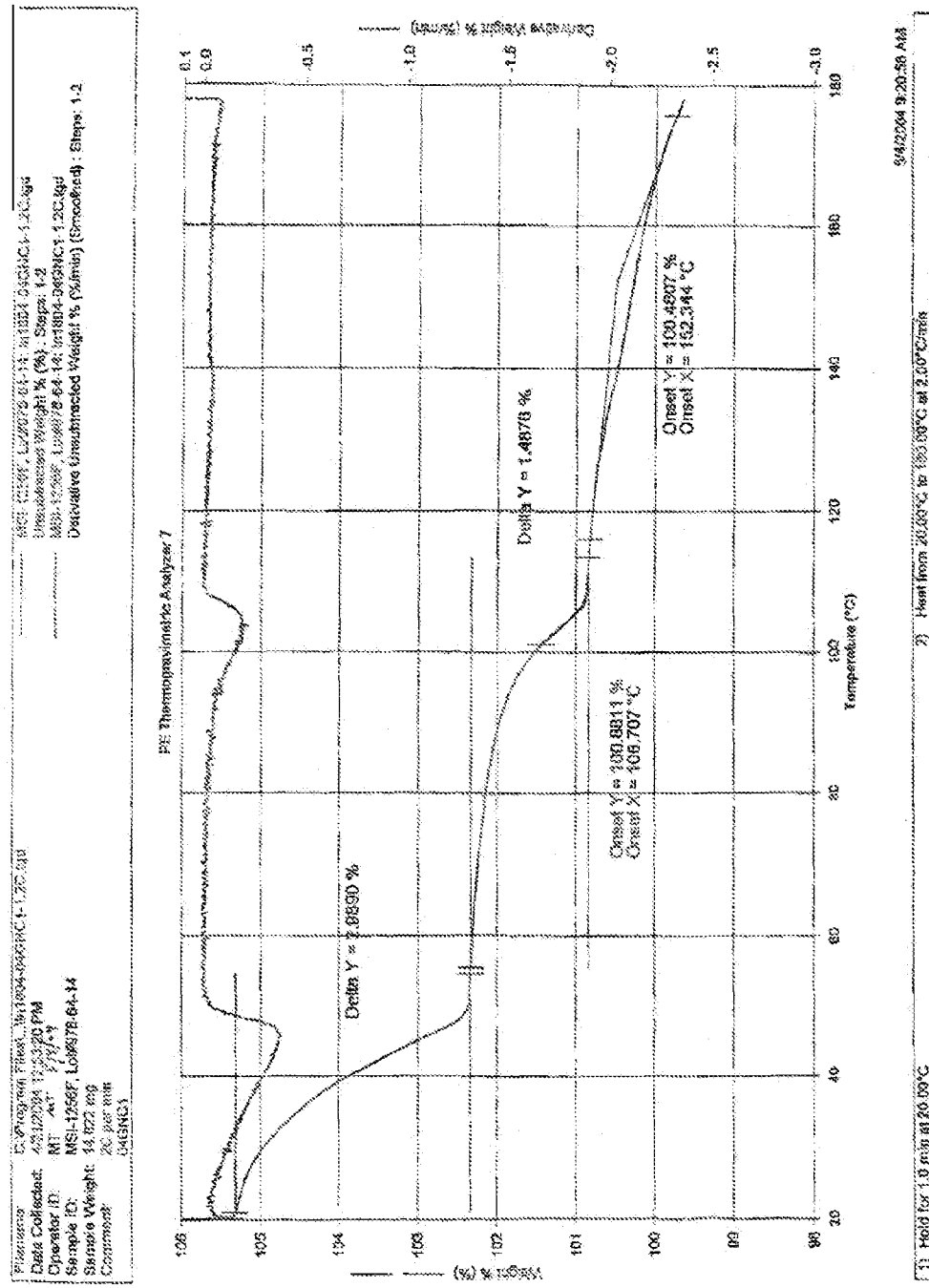
FIG. 10 shows a thermogravimetric scan of the squalamine dilactate crystallized from ethanol.

Thermogravimetric analysis involves the determination of the weight of a specimen as a function of temperature as per USP <891>. The samples were prepared in a nitrogen atmosphere in a humidity controlled glovebox. Analyses were completed using a Perkin Elmer TGA7 with TAC 7/DX Instrument Controller and Pyris Software Version 4.01. Nitrogen, NF was used at a flow rate of 20 mL/minute. The samples were warmed at a controlled rate of 10° C. per minute to generate better sensitivity and at 2° C. per minute in order to acquire a better resolution to a final temperature of 180° C. This squalamine dilactate sample had two distinct volatile weight loss events. The initial event yielded a 2.99% weight loss. The second event yielded an average weight loss of 1.49% with a peak event observed at a temperature of 106.7° C. when tested at 2° C. per minute. The total weight loss incurred by the sample was 4.48%. The two distinct weight loss events suggest that a bound form of water existed within the sample matrix. The initial loss is most likely due to the driving off of volatile constituents adsorbed to the material surface. The second weight loss event occurred due to a release of absorbed water associated with the sample matrix, which was most likely a crystalline hydrate, at a peak temperature of 106.7° C. The second distinct release of moisture from the sample at a specific temperature suggests a breakdown of a large portion of crystalline material. Temperatures relating to the onset of degradation were determined as well using TGA. The average onset to degradation temperature for this sample material was 152.3° C. The results for the 2° C. per minute scan are shown in FIG. 10 and the data summarized in the table below.

| Squalamine Dilactate Preparation | Rate (° C./min) | Primary Mass Loss | Peak of Secondary Mass Loss | Secondary Mass Loss | Onset to Degradation |
|---|---|---|---|---|---|
| Crystallized from ethanol/water | 2 | 2.99% | 106.7° C. | 1.49% | 152.3° C. |

Differential Scanning Calorimetry

Figure 11:
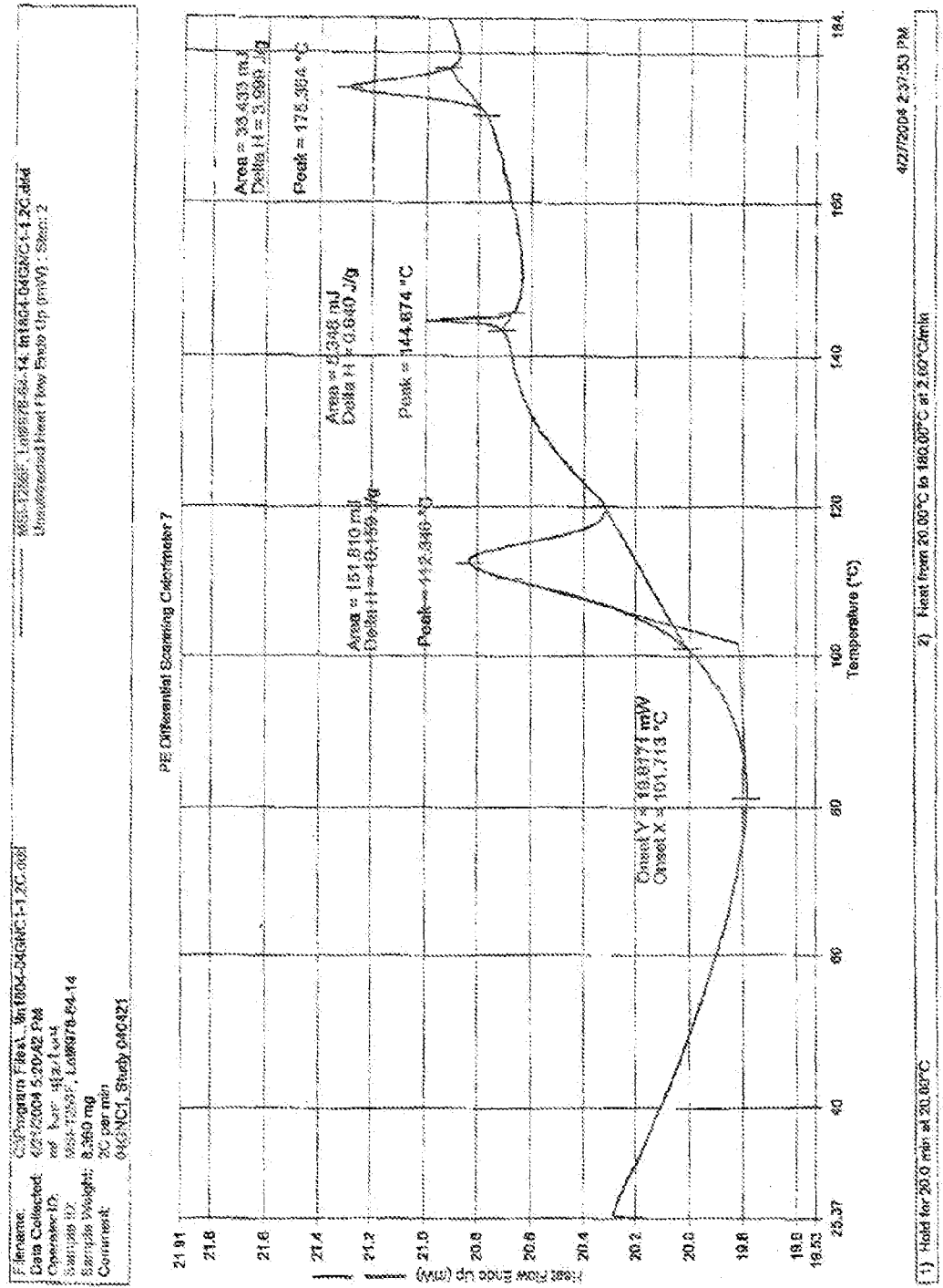
FIG. 11 shows a Differential Scanning calorimeter profile for squalamine dilactate crystallized from ethanol.

Samples were analyzed by high temperature differential scanning calorimetry and were run at 2° C. and 10° C. per minute. Thermal transitions acquired during a scan rate of 2° C. per minute are considered to be more accurate and are the calculations reflected in the conclusion. All events listed are endothermic peak temperatures unless otherwise noted. Examples of additional events include an "Exo" indicating an exothermic event or "Tg'" which indicates a phase transition. The lack of a notable thermal event on a particular scan is indicated by "none". The first and most significant thermal event characterized by DSC at 2° C. per minute for this material, was an endothermic event that occurred at a temperature of 112.3° C. Endothermic events are attributable to the initial melt of a crystalline material. This endothermic event coincides with the peak weight loss temperature of 106.7° C. during the TGA scan of this particular material. Two additional exothermic events were detected at temperatures of 144.7° C. and 175.4° C. The endothermic events, occurring at the temperatures of 141.1° C. and 151.6° C. during a scan at 10° C. per minute, did not have a corresponding thermal event when scanned at 2° C. per minute. The thermal events observed during the scan of the material indicate the melt of crystalline material. The most significant endothermic event observed during the 2° C. per minute scan of the material, occurring at a peak temperature of 112.4° C., resulted in a change in specific heat of 18.16 J/g. The change in specific heat associated with an endothermic event is correlated to the amount of energy required to melt that material. Therefore, the endothermic event, occurring the temperature of 112.4° C. is considered to represent the most stable crystalline material present. The results of the 2° C. per minute scan are shown in FIG. 11 and summarized in the table below.

| Squalamine Dilactate Preparation | Rate (° C./min) | 1 | 2 | 3 | 4 | 5 |
|---|---|---|---|---|---|---|
| Crystallized from ethanol/water | 2 | 112.3 | None | 144.7 | None | 175.4 |
| | 10 | 114.6 | 141.1 | 147.4 | 151.6 | 173.1 |

Example 6

Stability of Crystalline Squalamine Dilactate Precipitated from Ethanol

Samples of amorphous squalamine dilactate and squalamine dilactate recrystallized from ethanol as described in Example 5 were placed in scintillation vials and heated in an oven at 70° C. for three days. A portion of each heat stressed sample was then analyzed by HPLC with ELSD detection and the results compared with the HPLC analysis of unstressed material. The result of the HPLC analysis is shown in the table below.

| Material | 24 S Isomer | Squalamine | Lactylamide | Unknown | Unknown |
|---|---|---|---|---|---|
| Amorphous Squalamine Unstressed | 0.833% | 98.978% | 0.115% | 0.054% | 0.020% |
| Amorphous Squalamine Heat Stressed | 0.864% | 98.530% | 0.519% | 0.052% | 0.034% |
| Crystallized Squalamine Unstressed | 0.715% | 99.187% | 0.070% | 0.032% | <0.02% |
| Crystallized Squalamine Heat Stressed | 0.714% | 99.168% | 0.087% | 0.031% | <0.02% |

The result demonstrates a significant increase in the percentage of the lactylamide impurity when the amorphous squalamine is heat stressed but no significant increase in the crystallized material. We therefore conclude that recrystallization of squalamine dilactate is a method for improving the stability of the material. This improved stability is advantageous in the preparation and storage of the crystalline squalamine dilactate salt and its various formulations.

Example 7

Preparation of Crystalline Squalamine Dilactate from 2-Butanol

A supersaturated solution of amorphous squalamine dilactate was produced by heating an excess of squalamine dilactate to 90° C. in a mixture of 10 ml of 2-butanol plus 100 µl of water. The excess squalamine dilactate was filtered off and the solution was cooled to −20° C. A precipitate of white needles formed, the supernatant was removed and the solid dried in a vacuum desiccator.

X-Ray Diffraction Powder Pattern

Figure 12:
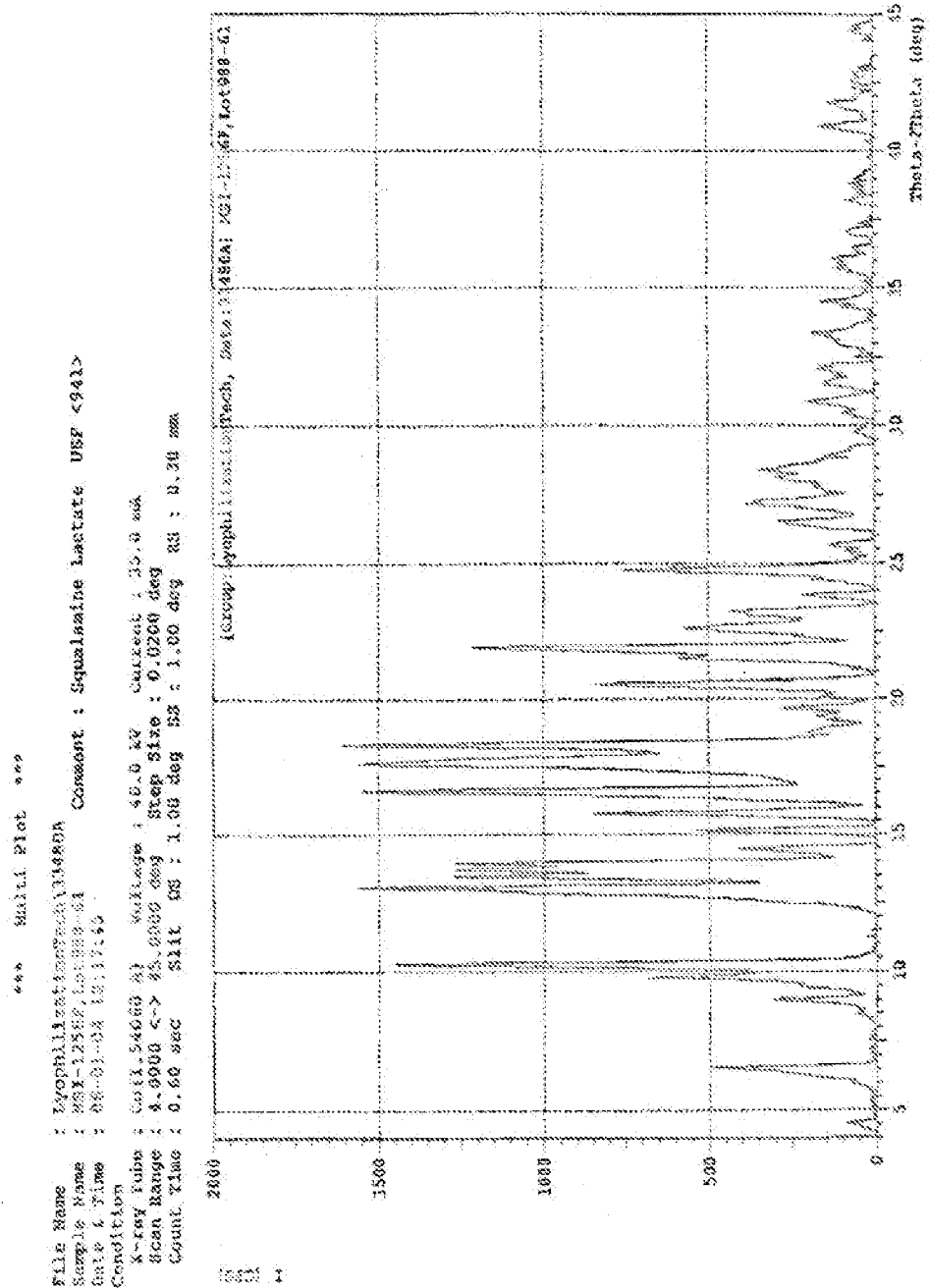
FIG. 12 shows the x-ray diffraction powder pattern for squalamine dilactate crystallized from 2-butanol.

The powder x-ray diffraction scans on a sample of squalamine dilactate crystallized from 2-butanol were performed from 4.0 to 45.0 degrees (2θ, in compliance with USP Method <941>) while the sample was covered by a polycarbonate film. The pertinent data, consisting of distinct crystalline peaks is shown in FIG. 12 and summarized in the table below and indicates a crystalline material.

| Sample Preparation | Angle (° theta-2 theta) | | |
|---|---|---|---|
| | 13.1 | 17.7 | 18.3 |
| Crystallized from 2-butanol/water | 939 | 937 | 967 |

Thermogravimetric Analysis

Figure 13:
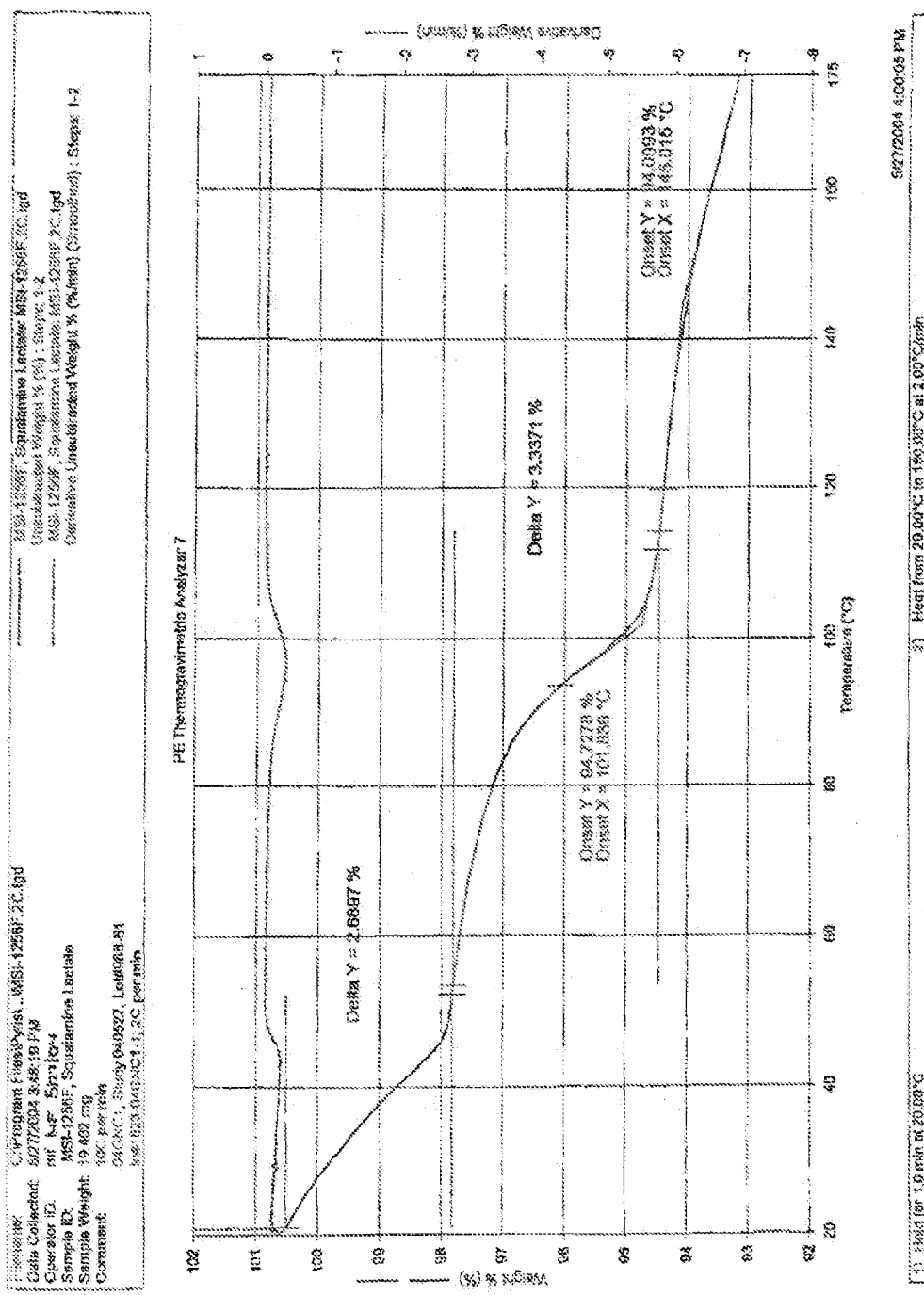
FIG. 13 shows a thermogravimetric scan of the squalamine dilactate crystallized from 2-butanol.

Thermogravimetric analysis involves the determination of the weight of a specimen as a function of temperature as per USP <891>. The samples were prepared in a nitrogen atmosphere in a humidity controlled glovebox. Analyses were completed using a Perkin Elmer TGA7 with TAC 7/DX Instrument Controller and Pyris Software Version 4.01. Nitrogen, NF was used at a flow rate of 20 mL/minute. The samples were warmed at a controlled rate of 10° C. per minute to generate better sensitivity and at 2° C. per minute in order to acquire a better resolution to a final temperature of 180° C. This squalamine dilactate sample had two distinct volatile weight loss events. The initial event yielded a 2.69% weight loss. The second event yielded an average weight loss of 3.34% with a peak event observed at a temperature of 101.8° C. when tested at 2° C. per minute. The total weight loss incurred by the sample was 6.03%. The two distinct weight loss events suggest that a bound form of solvent existed within the sample matrix. The initial loss is most likely due to the driving off of volatile constituents adsorbed to the material surface. The second weight loss event occurred due to a release of absorbed water associated with the sample matrix, which was most likely a crystalline hydrate, at a peak temperature of 101.8° C. The second distinct release of moisture from the sample at a specific temperature suggests a breakdown of a large portion of crystalline material. Temperatures relating to the onset of degradation were determined as well using TGA. The average onset to degradation temperature for this sample material was 145.0° C. The results for the 2° C. per minute scan are shown in FIG. 13 and the data summarized in the table below.

| Squalamine Dilactate Preparation | Rate (° C./min) | Primary Mass Loss | Peak of Secondary Mass Loss | Secondary Mass Loss | Onset to Degradation |
|---|---|---|---|---|---|
| Crystallized from 2-butanol/water | 2 | 2.69% | 101.8° C. | 3.34% | 145.0° C. |

Differential Scanning Calorimetry

Figure 14:
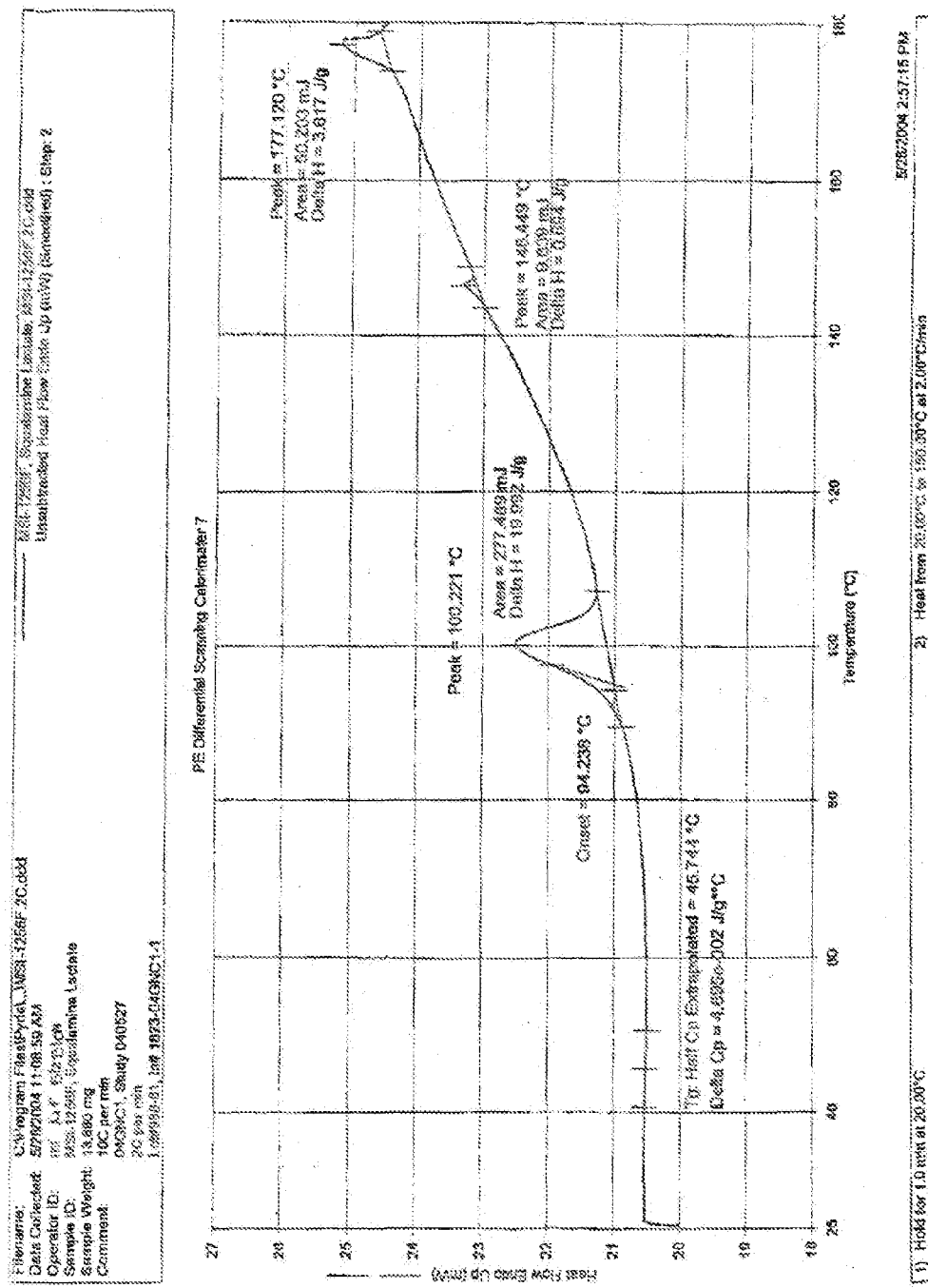
FIG. 14 shows a Differential Scanning calorimeter profile for squalamine dilactate crystallized from 2-butanol.

Samples were analyzed by high temperature differential scanning calorimetry and were run at 2° and 10° C. per minute. Thermal transitions acquired during a scan rate of 2° C. per minute are considered to be more accurate and are the calculations reflected in the conclusion. All events listed are endothermic peak temperatures unless otherwise noted. Examples of additional events include an "Exo" indicating an exothermic event or "Tg" which indicates a phase transition. The lack of a notable thermal event on a particular scan is indicated by "none". The first thermal event characterized by DSC at 2° C. per minute for this material, was a glass transition (Tg) event that occurred at a temperature of 45.7° C. A glass transition event is often attributed to some amount of amorphous material. An endothermic event was detected at a temperature of 100.2° C., resulting in a change in specific heat of 19.99 J/g. Endothermic events are attributable to the initial melt of a crystallized material. The change in specific heat associated with an endothermic event is correlated to the amount of energy required to melt that material. This endothermic event coincides with the peak weight loss temperature of 101.8° C. during the TGA scan of this particular material. Therefore, the endothermic event, occurring the temperature of 100.2° C. is considered to represent the most stable crystalline material present. Two additional exothermic events were detected at temperatures of 146.4° and 177.1° C. The endothermic event, occurring at the temperatures of 153.8° during a scan at 10° C. per minute, did not have a corresponding thermal event when scanned at 2° C. per minute. The results of the 2° C. per minute scan are shown in FIG. 14 and summarized in the table below.

| Squalamine Dilactate Preparation | Rate (° C./min) | 1 | 2 | 3 | 4 | 5 |
|---|---|---|---|---|---|---|
| Crystallized from 2-butanol/water | 2 | 45.7 (Tg) | 100.2 | 146.4 | None | 177.1 |
| | 10 | 42.2 (Tg) | 103.2 | 146.1 | 153.8 | 179.8 (onset) |

Example 8

Improved Method for the Manufacturing of Crystalline Squalamine Dilactate

Compound 36 was prepared according to the methods described in U.S. Pat. Nos. 6,262,283 and 6,610,866 and U.S. patent application Ser. No. 10/268,660. Approximately 490.0 gms. (2.0 Moles) of azidospermidine dihydrochloride was dissolved in 22.5 L of pyridine at ambient temperature. Approximately 8.0 L (4.0 Moles) of a 0.5 M solution of sodium methoxide-methanol solution was added and the mixture was stirred for about 0.5 hours. Approximately 641.0 gms. (1.0 Mole) of compound 36 was added and the reaction mixture stirred for an additional two hours. The reaction mixture was concentrated to dryness in vacuo (max. 43°

Figure 15:
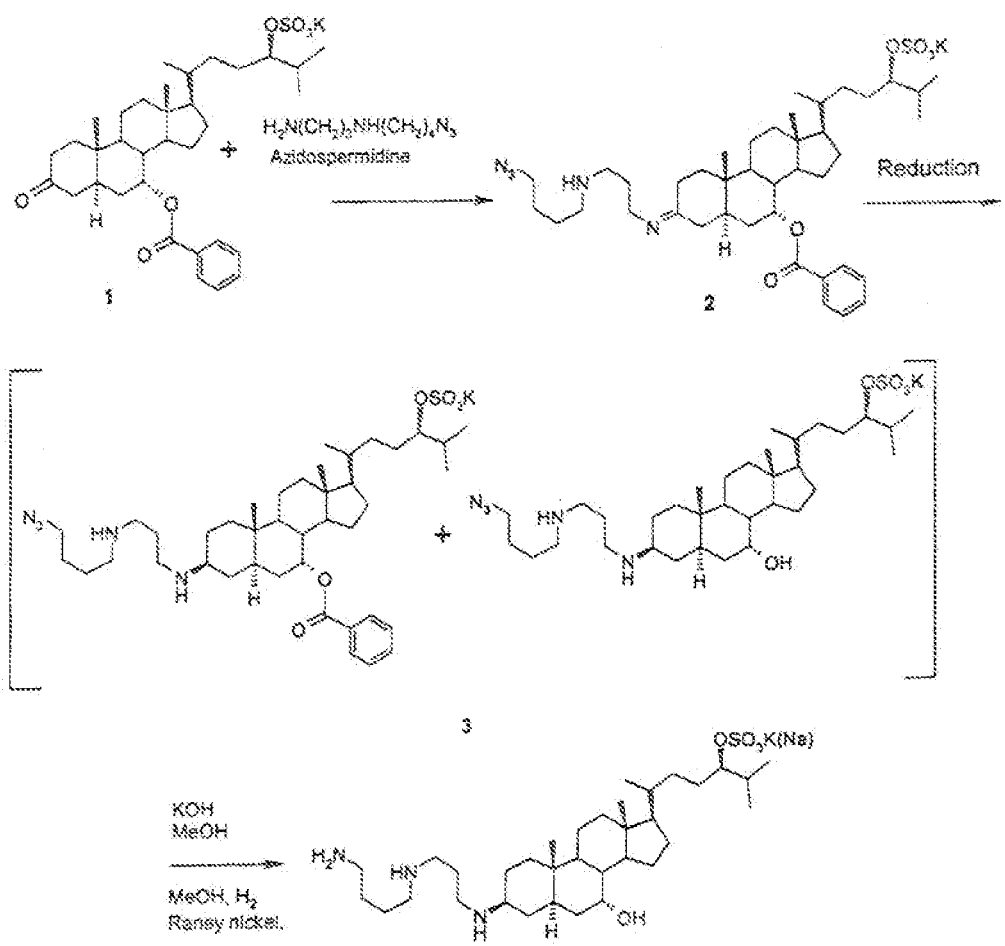
FIG. 15 shows a scheme depicting a new method for the production of squalamine.

C./171 mbar) to remove water, approximately 11.28 L of pyridine was added and the solvent was again distilled off in vacuo. (max. 43° C./171 mbar). Approximately 22.5 L of methanol was added and the obtained suspension cooled to less than about −75° C. Approximately 114 gms. (3.0 Moles) of sodium borohydride was added and the reaction mixture was stirred at less than about −75° C. until compound 36 was transformed as analyzed by HPLC. The mixture was heated to about 15 to about 25° C. and then 2.7 L of distilled water was added to the solution. The solution was concentrated at reduced pressure and a temperature of less than 65° C. to a final volume of about 26.8 L. Approximately 13.4 L of 2-Butanol was added and the mixture stirred before allowing the layers to separate. The lower aqueous layer was removed for disposal at the completion of the batch. (If there is no separation, add MTBE (up to 5 L) to the mixture to aid in separating layers.) The organic phase was washed with 2.7 L of distilled water, the aqueous phase back washed with 17.2 L of 2-Butanol and the two 2-Butanol phases combined. The organic portion, crude compound 40, was concentrated to dryness in vacuo to be used for the preparation of squalamine without further purification. Approximately 796.18 gms. (1.0 Mole) of crude compound 40 was dissolved in 5.7 L of methanol and approximately 280 gms. (5.0 Moles) of potassium hydroxide was added. The reaction mixture was heated at reflux (about 64° C.) until all of the Compound 40 was consumed. Approximately 198 gms. of Raney Nickel catalyst was added and the reaction mixture was hydrogenated at a temperature of 15-25° C. under 2-3 bars of hydrogen pressure until Compound 38 was consumed as analyzed by TLC. The reaction mixture was filtered to remove the catalyst using Celite 545 as a filter aid. The filter cake was washed two times with 800 mL methanol and the combined filtrate and washes were concentrated in vacuo at a temperature of less than about 60° C. to a volume of 6.7 L. Approximately 18.8 L of 2-Butanol was added to the concentrated solution and the solution concentrated under reduced pressure at less than about 60° C. to about 5.36 L. Approximately 13.4 L of methyl t-butyl ether was added and the solution cooled to less than about −5° C. The precipitated product was collected, the filter cake washed two times with 1.3 L of methyl t-butyl ether and the product dried under vacuum at about 25 to about 35° C. A total of 490 gms. of crude squalamine was obtained representing a yield of 75.5%. The synthesis scheme for crude squalamine is shown in FIG. 15.

Figure 16:
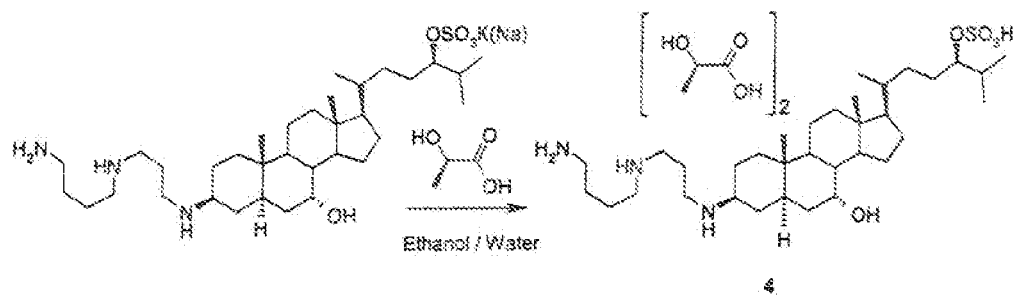
FIG. 16 shows a scheme depicting a new method for the production of squalamine dilactate.

Recrystallization: Approximately 650 gms. (1.0 Mole) of crude squalamine was mixed into 11.05 L of ethanol to form a cloudy solution. The solution was filtered through a filter coated with filter aid and the filter cake washed with 650 ml. of ethanol. Approximately 494 ml of water and approximately 360.3 gms. (4.0 Moles) of L-(+) Lactic Acid was added to the filtered solution with stirring. The resulting solution was filtered through a 0.22 gm filter and the container and filter washed with 650 ml. of ethanol. The filtrate was cooled to about 0 to about 5° C. for at least 12 hours without stirring and then approximately 100 mg of recrystallized squalamine dilactate seed crystals were added. The solution was maintained at about 0 to about 5° C. without stirring for at least 48 more hours and then the resulting precipitation was agitated at less than about 5° C. to form a homogeneous suspension. The solids were collected and the filter cake washed with 650 ml. of cold (0 to 5° C.) ethanol. The product was dried in vacuo at about 40° C. (±2° C.) to yield a total of 614 g (76.0% yield) of crystallized squalamine dilactate. The synthesis scheme for crude squalamine dilactate is shown in FIG. 16.

Approximately 1 kg. of crystallized or recrystallized squalamine dilactate was combined with 18 L. of ethanol and 760 ml. of water. The suspension was heated to about 40 to about 50° C. with stirring to form a solution and then filtered through a 0.22 μm filter. The container and filter were washed with 1 L. of ethanol and the total filtrate cooled to 20° C. (±2° C.) for at least about twelve hours. Approximately 100 mg of recrystallized squalamine dilactate seed crystals were added the solution was maintained at about 20° C. (±2° C.) without stirring for at least 48 more hours. The resulting precipitation was agitated to form a homogeneous suspension and the solids collected. The filter cake was washed with 1.0 L. of cold (0 to 5° C.) ethanol and the product dried in vacuo at about 40° C. (±2° C.) to yield a total of 900 gms (90.0% yield) of recrystallized squalamine di lactate.

The analysis of the crystalline squalamine dilactate produced by this process is shown in the table below.

| Test | Specification | Results |
| --- | --- | --- |
| HPLC Purity | >95.00% | 99.0% |
| 24-S | ≤1.7% | 0.74% |
| 3-α | ≤0.1% | <0.1% |
| Lactyl Amide | <1.5% | 0.17% |
| Des-Sulfate | ≤0.1% | <0.1% |
| Lactic Acid | <30% | 22.89% |
| Water by Karl Fischer | <10% | 2.18% |
| HPLC MS | 628 ± 1amu | Conforms |
| NMR | Conforms to ref. | Conforms |
| FTIR | Conforms to ref. | Conforms |
| XRD | No specification | Completed |
| DSC | No specification | Mp 143.9° Purity 99.99% |
| Residual solvents (Ethanol) | 5000 ppm | <200 ppm |
| Sodium | No specification | 80.5 mg/kg |
| Potassium | No specification | 520 mg/kg |

Figure 17:
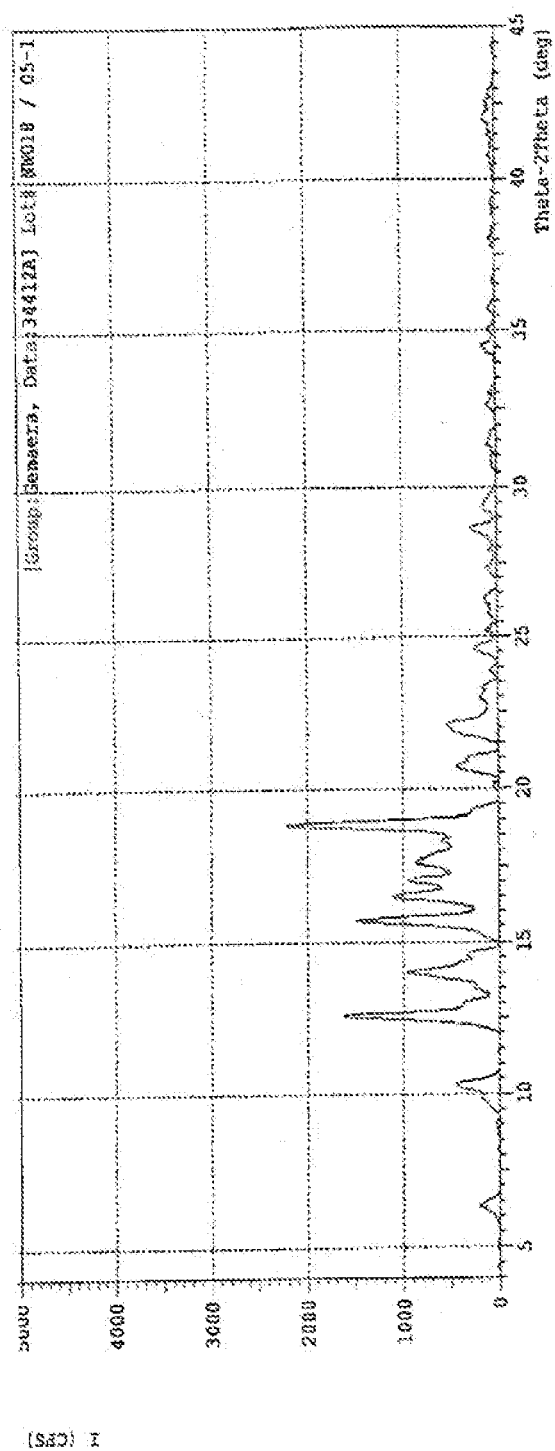
FIG. 17 shows the x-ray diffraction powder pattern for recrystallized squalamine dilactate produced by the newly described synthesis of squalamine dilactate.

The X-ray diffraction powder pattern, which was determined as described in Example 1 above, is shown in FIG. 17 and the intensity of the major peaks is shown in the table below.

| | Angle (° theta-2 theta) | | |
| --- | --- | --- | --- |
| Sample Preparation | 12.6 | 15.7 | 18.8 |
| Crystallized from ethanol/water in the squalamine manufacturing process | 977 | 891 | 1333 |

The powder pattern indicates that even though the squalamine dilactate was recrystallized from ethanol/water as in Example 5, a different polymorphic form has been produced (compare FIGS. 9 and 17). This is likely due to the use of 4% water in the manufacturing process as opposed to 1% water in Example 5 and the fact that the material was crystallized at 20° C. instead of −20° C. There is also evidence from the Karl Fisher titration that the recrystallized material from the manufacturing process is a monohydrate. This new manufacturing process also produces a better yield and a purer product than the process described in U.S. Pat. No. 6,262,283.

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. All patents, patent applications and other references cited throughout this application are herein incorporated by reference in their entirety.

We claim:

1. An isolated amorphous form of the dilactate salt of 3β-(N-[3-aminopropyl]-1,4-butanediamine)-7α,24R-dihydroxy-5α-cholestane-24-sulfate wherein an X-ray powder diffraction pattern of the salt has major diffraction angles of 15.5 to 15.6 degrees, 17.3 to 17.5 degrees and 21.3 to 21.5 degrees with relative peak intensities of 286, 391, and 107, respectively.

2. The dilactate salt according to claim 1, wherein the dilactate salt has a low crystallinity.

3. The dilactate salt according to claim 1, wherein the dilactate salt is partially crystalline.

4. A pharmaceutical composition comprising the amorphous form of the dilactate salt according to any one of claims 1 and 2 and a pharmaceutically acceptable carrier.

* * * * *